(12) United States Patent
Willoughby et al.

(10) Patent No.: US 9,561,350 B2
(45) Date of Patent: Feb. 7, 2017

(54) PARANASAL SINUS ACCESS IMPLANT DEVICES AND RELATED TOOLS, METHODS AND KITS

(71) Applicant: Sinopsys Surgical, Inc., Boulder, CO (US)

(72) Inventors: Brian James Willoughby, Denver, CO (US); Christopher Lee Oliver, Lakewood, CO (US); Harry Ross, Boulder, CO (US); William W. Cimino, Louisville, CO (US)

(73) Assignee: SINOPSYS SURGICAL, INC., Boulder, CO (US)

( * ) Notice: Subject to any disclaimer, the term of this patent is extended or adjusted under 35 U.S.C. 154(b) by 0 days.

(21) Appl. No.: 14/424,841

(22) PCT Filed: Jan. 24, 2014

(86) PCT No.: PCT/US2014/012995
§ 371 (c)(1),
(2) Date: Feb. 27, 2015

(87) PCT Pub. No.: WO2014/116980
PCT Pub. Date: Jul. 31, 2014

(65) Prior Publication Data
US 2015/0231376 A1 Aug. 20, 2015

Related U.S. Application Data

(60) Provisional application No. 61/757,046, filed on Jan. 25, 2013, provisional application No. 61/891,250, filed on Oct. 15, 2013.

(51) Int. Cl.
*A61M 5/00* (2006.01)
*A61M 27/00* (2006.01)
(Continued)

(52) U.S. Cl.
CPC ........ *A61M 27/002* (2013.01); *A61F 9/00772* (2013.01); *A61B 17/24* (2013.01); *A61K 9/0051* (2013.01); *A61M 29/02* (2013.01)

(58) Field of Classification Search
CPC .................. A61F 9/00772; A61F 2250/00067; A61F 9/00781; A61K 9/0051; A61M 27/002; A61M 29/02; A61B 17/24
See application file for complete search history.

(56) References Cited

U.S. PATENT DOCUMENTS

| 3,726,284 A | 4/1973 | Parker |
| 3,948,272 A | 4/1976 | Guibor |

(Continued)

FOREIGN PATENT DOCUMENTS

| CN | 1735436 A | 2/2006 |
| EP | 0631793 A1 | 1/1995 |

(Continued)

OTHER PUBLICATIONS

Ex Parte Kamrava, Appeal 2010-010201, U.S. Appl. No. 10/080,177.*

(Continued)

*Primary Examiner* — Tatyana Zalukaeva
*Assistant Examiner* — Ariana Zimbouski
(74) *Attorney, Agent, or Firm* — Marsh Fischmann & Breyfogle LLP; Ross E. Breyfogle

(57) ABSTRACT

A paranasal sinus access implant device to provide an artificial fluid path in fluid communication with the lacrimal apparatus may be implanted through a fistula opening into the lacrimal apparatus. The implant device may have a conduit with a first longitudinal portion having a larger minimum wall thickness than a minimum wall thickness of a second a second longitudinal portion of the conduit located distal of the first longitudinal portion. Various kits may (Continued)

include a paranasal sinus access implant device and one of more other components for a procedure involving implantation. A method involves use of a cutting tool to cut away tissue to prepare a fistula sized for implantation.

38 Claims, 20 Drawing Sheets

(51) Int. Cl.
 *A61F 9/007* (2006.01)
 *A61B 17/24* (2006.01)
 *A61K 9/00* (2006.01)
 *A61M 29/02* (2006.01)

(56) References Cited

U.S. PATENT DOCUMENTS

| | | | |
|---|---|---|---|
| 4,915,684 A | 4/1990 | MacKeen et al. | |
| 4,921,485 A | 5/1990 | Griffiths | |
| 5,169,386 A | 12/1992 | Becker et al. | |
| 5,345,948 A | 9/1994 | O'Donnell, Jr. | |
| 6,041,785 A | 3/2000 | Webb | |
| 6,083,188 A | 7/2000 | Becker | |
| 6,629,533 B1* | 10/2003 | Webb | A61B 17/12022 128/887 |
| 6,878,165 B2 | 4/2005 | Makino | |
| 6,966,888 B2 | 11/2005 | Cullen et al. | |
| 7,156,821 B2 | 1/2007 | Dohlman | |
| 7,169,163 B2 | 1/2007 | Becker | |
| 7,361,168 B2 | 4/2008 | Makower et al. | |
| 7,410,480 B2 | 8/2008 | Muni et al. | |
| 7,419,497 B2 | 9/2008 | Muni et al. | |
| 7,462,175 B2 | 12/2008 | Chang et al. | |
| 7,500,971 B2 | 3/2009 | Chang et al. | |
| D590,935 S | 4/2009 | Becker | |
| 7,547,323 B2 | 6/2009 | Lavigne | |
| 7,559,925 B2 | 7/2009 | Goldfarb et al. | |
| 7,641,644 B2 | 1/2010 | Chang et al. | |
| 7,645,272 B2 | 1/2010 | Chang et al. | |
| 7,654,997 B2 | 2/2010 | Makower et al. | |
| 7,713,255 B2 | 5/2010 | Eaton et al. | |
| 7,720,521 B2 | 5/2010 | Chang et al. | |
| 7,727,186 B2 | 6/2010 | Makower et al. | |
| 7,727,226 B2 | 6/2010 | Chang et al. | |
| 7,758,534 B2 | 7/2010 | Pearson | |
| 7,771,409 B2 | 8/2010 | Chang et al. | |
| 7,785,315 B1 | 8/2010 | Muni et al. | |
| 7,803,150 B2 | 9/2010 | Chang et al. | |
| 7,846,124 B2 | 12/2010 | Becker | |
| 9,022,967 B2 | 5/2015 | Oliver et al. | |
| 2002/0032444 A1 | 3/2002 | Mische | |
| 2002/0107579 A1 | 8/2002 | Makino | |
| 2004/0077989 A1 | 4/2004 | Goode et al. | |
| 2004/0116958 A1 | 6/2004 | Gopferich et al. | |
| 2004/0204704 A1 | 10/2004 | Tamplenizza et al. | |
| 2004/0254516 A1* | 12/2004 | Murray | A61F 9/00772 604/8 |
| 2005/0197614 A1 | 9/2005 | Pritchard et al. | |
| 2005/0240143 A1 | 10/2005 | Dohlman | |
| 2005/0245906 A1 | 11/2005 | Makower et al. | |
| 2005/0273033 A1 | 12/2005 | Grahn et al. | |
| 2006/0063973 A1 | 3/2006 | Makower et al. | |
| 2006/0142736 A1 | 6/2006 | Hissink et al. | |
| 2006/0251575 A1 | 11/2006 | Morgenstern | |
| 2006/0276738 A1 | 12/2006 | Becker | |
| 2007/0005120 A1 | 1/2007 | Villacampa et al. | |
| 2007/0112291 A1 | 5/2007 | Borgesen | |
| 2007/0129751 A1 | 6/2007 | Muni et al. | |
| 2007/0135789 A1 | 6/2007 | Chang et al. | |
| 2007/0167682 A1 | 7/2007 | Goldfarb et al. | |
| 2007/0208252 A1 | 9/2007 | Makower | |
| 2007/0208301 A1 | 9/2007 | Evard et al. | |
| 2007/0249896 A1 | 10/2007 | Goldfarb et al. | |
| 2007/0255263 A1 | 11/2007 | Sugimoto | |
| 2007/0269487 A1 | 11/2007 | De Juan et al. | |
| 2007/0276314 A1 | 11/2007 | Becker | |
| 2007/0282305 A1 | 12/2007 | Goldfarb et al. | |
| 2007/0293726 A1 | 12/2007 | Goldfarb et al. | |
| 2007/0293727 A1 | 12/2007 | Goldfarb et al. | |
| 2008/0082037 A1 | 4/2008 | Pearson | |
| 2008/0097154 A1 | 4/2008 | Makower et al. | |
| 2008/0097354 A1 | 4/2008 | Lavigne | |
| 2008/0097514 A1 | 4/2008 | Chang et al. | |
| 2008/0103361 A1 | 5/2008 | Makower et al. | |
| 2008/0103521 A1 | 5/2008 | Makower et al. | |
| 2008/0119693 A1 | 5/2008 | Makower et al. | |
| 2008/0125626 A1 | 5/2008 | Chang et al. | |
| 2008/0125805 A1 | 5/2008 | Mische | |
| 2008/0132938 A1 | 6/2008 | Chang et al. | |
| 2008/0154237 A1 | 6/2008 | Chang et al. | |
| 2008/0154250 A1 | 6/2008 | Makower et al. | |
| 2008/0195041 A1 | 8/2008 | Goldfarb et al. | |
| 2008/0228085 A1 | 9/2008 | Jenkins et al. | |
| 2008/0234720 A1 | 9/2008 | Chang et al. | |
| 2008/0275483 A1 | 11/2008 | Makower et al. | |
| 2008/0281156 A1 | 11/2008 | Makower et al. | |
| 2008/0287908 A1 | 11/2008 | Muni et al. | |
| 2008/0306428 A1 | 12/2008 | Becker | |
| 2008/0319424 A1 | 12/2008 | Muni et al. | |
| 2009/0005763 A1 | 1/2009 | Makower et al. | |
| 2009/0028923 A1 | 1/2009 | Muni et al. | |
| 2009/0030274 A1 | 1/2009 | Goldfarb et al. | |
| 2009/0036818 A1 | 2/2009 | Grahn et al. | |
| 2009/0099626 A1 | 4/2009 | de Juan, Jr. et al. | |
| 2009/0104248 A1* | 4/2009 | Rapacki | A61F 9/0017 424/427 |
| 2009/0105749 A1 | 4/2009 | de Juan et al. | |
| 2009/0187098 A1 | 7/2009 | Makower et al. | |
| 2009/0198216 A1 | 8/2009 | Muni et al. | |
| 2009/0204142 A1 | 8/2009 | Becker et al. | |
| 2009/0221988 A1 | 9/2009 | Ressemann et al. | |
| 2009/0240112 A1 | 9/2009 | Goldfarb et al. | |
| 2009/0240237 A1 | 9/2009 | Goldfarb et al. | |
| 2009/0275882 A1 | 11/2009 | Lavigne | |
| 2009/0275903 A1 | 11/2009 | Lavigne | |
| 2009/0281621 A1 | 11/2009 | Becker | |
| 2009/0312745 A1 | 12/2009 | Goldfarb et al. | |
| 2010/0034870 A1 | 2/2010 | Sim et al. | |
| 2010/0042046 A1 | 2/2010 | Chang et al. | |
| 2010/0076269 A1 | 3/2010 | Makower et al. | |
| 2010/0099946 A1 | 4/2010 | Jenkins et al. | |
| 2010/0100181 A1 | 4/2010 | Makower et al. | |
| 2010/0106255 A1 | 4/2010 | Dubin | |
| 2010/0114066 A1 | 5/2010 | Makower et al. | |
| 2010/0121308 A1 | 5/2010 | Muni et al. | |
| 2010/0174138 A1 | 7/2010 | Chang et al. | |
| 2010/0174308 A1 | 7/2010 | Chang et al. | |
| 2010/0198247 A1 | 8/2010 | Chang et al. | |
| 2010/0210901 A1 | 8/2010 | Makower et al. | |
| 2010/0268245 A1 | 10/2010 | Chang et al. | |
| 2010/0274204 A1 | 10/2010 | Rapacki et al. | |
| 2010/0298862 A1 | 11/2010 | Chang et al. | |
| 2010/0317969 A1 | 12/2010 | Becker | |
| 2011/0004057 A1 | 1/2011 | Goldfarb et al. | |
| 2011/0060214 A1 | 3/2011 | Makower | |
| 2011/0105989 A1 | 5/2011 | Becker | |
| 2011/0112512 A1 | 5/2011 | Muni et al. | |
| 2011/0224680 A1 | 9/2011 | Barker | |
| 2011/0276131 A1 | 11/2011 | De Juan, Jr. et al. | |
| 2012/0089071 A1* | 4/2012 | Oliver | A61F 9/00772 604/8 |
| 2012/0245539 A1 | 9/2012 | Zarins et al. | |
| 2013/0030545 A1 | 1/2013 | Gross et al. | |
| 2013/0231693 A1 | 9/2013 | Edgren et al. | |
| 2013/0274647 A1 | 10/2013 | Oliver et al. | |
| 2014/0012309 A1 | 1/2014 | Keith et al. | |
| 2015/0065941 A1 | 3/2015 | Ross et al. | |

FOREIGN PATENT DOCUMENTS

| | | |
|---|---|---|
| FR | 2813522 A1 | 3/2002 |
| WO | 2009035562 A2 | 3/2009 |
| WO | 2009145755 A1 | 12/2009 |

(56) References Cited

FOREIGN PATENT DOCUMENTS

| WO | 2010096822 A2 | 8/2010 |
|---|---|---|
| WO | 2010111528 A2 | 9/2010 |
| WO | 2011066479 A1 | 6/2011 |

OTHER PUBLICATIONS

Sadeghi, Nader, M.D. et al. Transnasal Endoscopic Medial Maxillectomy for Inverting Papilloma. Laryngoscope (2003) 113:749-753.

Dictionary Definition for 'inject'. hllps:l/www.google.com/search?q=inject&sourceid=ie7&rls=com.microsoft:en-us:IE-Address&ie=&oe=&gws_rd=ssl.

Mangan, BG et al. Bilateral Nasolacrimal Duct Atresia in a Cria. Veterinary Opthalmology (2008) 11, 1, 49-54.

Giuliano, EA et al. Dacryocystomaxillorhinostomy for Chronic Dacryocystitis in a Dog. Veterinary Opthalmology (2006) 9, 2, 89-94.

Wilson, DG et al. Surgical Reconstruction of the Nasolacrimal System in the Horse. Equine Veterinary Science (1991) vol. II, No. 4, pp. 232-234.

Steinmetz, A et al. Surgical Removal of a Dermoid Cyst From the Bony Part of Thenasolacrimal Duct in a Scottish Highland Cadle Heifer. Veterinary Opthalmology (2009) 12, 4, 259-262.

McIlnay, TR et al. Use of Canaliculorhinostomy for Repair of Nasolacrimal Duct Obstruction in a Horse. JAVMA (2001) vol. 218, No. 8. Scientific Reports: Clinical Report. 1323-1324.

Gionfriddo JR. The nasolacrimal system. In: Textbook of Small Animal Surgery 3rd edition. 2003, Slatter OM ed. Saunders, Philadelphia PA, pp. 1356-1358.

Bagdonaite, Laura, M.D. et al. "Twelve-Year Experience of Lester Jones Tubes—Results and Comparison of 3 Different Tube Types", Opthalmic Plastic Reconstructive Surgery (2015) vol. 31, No. 5., pp. 352-356.

\* cited by examiner

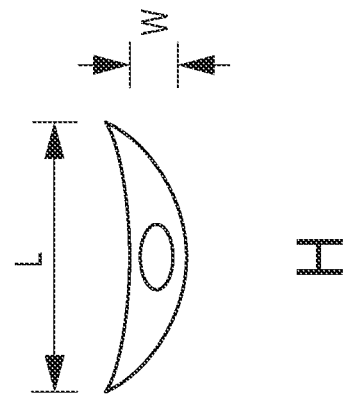
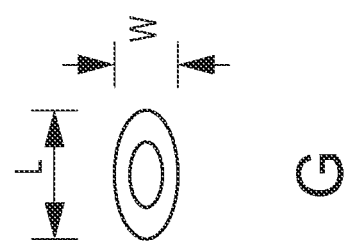
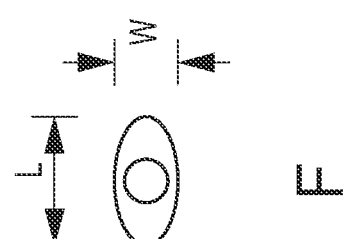
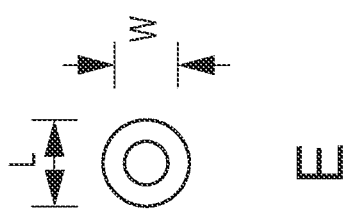
FIG. 9

PARANASAL SINUS ACCESS IMPLANT DEVICES AND RELATED TOOLS, METHODS AND KITS

CROSS-REFERENCE TO RELATED APPLICATIONS

This application claims the benefit of U.S. provisional patent application no. 61/757,046 entitled "IMPLANT DEVICE, METHOD AND KIT FOR IMPLANTATION BETWEEN THE LACRIMAL SYSTEM AND A PARANASAL SINUS" filed Jan. 25, 2013 and the benefit of U.S. provisional patent application No. 61/891,250 entitled "PARANASAL SINUS ACCESS IMPLANT DEVICES AND RELATED TOOLS, METHODS AND KITS" filed Oct. 15, 2013, the entire contents of each of which is incorporated by reference herein.

This application incorporates by reference each and every portion of the following: international patent application no. PCT/US2011/055456 entitled "IMPLANT DEVICE, TOOL, AND METHODS RELATING TO TREATMENT OF PARANASAL SINUSES" filed Oct. 7, 2011; U.S. nonprovisional patent application Ser. No. 13/225,213 entitled "IMPLANT DEVICE, TOOL, AND METHODS RELATING TO TREATMENT OF PARANASAL SINUSES" filed Sep. 2, 2011; U.S. provisional patent application No. 61/528,058 entitled "IMPLANT DEVICE, TOOL, AND METHODS RELATING TO TREATMENT OF PARANASAL SINUSES" filed Aug. 26, 2011; U.S. provisional patent application No. 61/404,716 entitled "METHODS AND TOOLS FOR TREATMENT AND PREVENTION OF SINUSITIS" filed Oct. 8, 2010; U.S. provisional patent application No. 61/623,022 entitled "IMPLANTATION TOOLS, TOOL ASSEMBLIES, KITS AND METHODS" filed Apr. 11, 2012; and international patent application no. PCT/US2013/03447 entitled "IMPLANTATION TOOLS, TOOL ASSEMBLIES, KITS AND METHODS" filed Mar. 28, 2013.

FIELD OF THE INVENTION

The invention relates to treatment of conditions of the paranasal sinuses, including with respect to paranasal sinus access implant devices, surgical tools, methods and kits.

BACKGROUND OF THE INVENTION

In the United States alone, 35 million people a year are treated for sinus infections, or sinusitis, and 7 million of those will suffer from chronic sinusitis and will have minimal response to prescription drug therapies. Conventional surgical interventions may be expected to, at best, offer only moderate symptomatic improvement but no cure.

Conventional drug therapies include oral administration as pills and nasal topical administration, neither of which is conducive to delivering adequate concentration of medication to the involved paranasal sinus. In addition to medication, frequent sinus irrigation can be helpful in flushing out debris, irritants and obstructing viscous fluids, but patients are generally not able to adequately perform this procedure at home.

For patients with particularly severe symptoms, surgical drainage has been an option of last resort. An early surgical procedure was the Caldwell-Luc procedure, which involves creating a permanent fistula from the base of the paranasal sinus into the oral cavity above the front upper incisors. More recently, other surgical access points to the paranasal sinuses have been attempted. A variety of endoscopic techniques have been developed that access the paranasal sinuses through the nose, including functional endoscopic sinus surgery (FESS) and balloon sinuplasty. All attempt to increase drainage, but utilize different routes or tools. Surgical formation of a fistula between the lacrimal apparatus and a paranasal sinus has been identified as a technique to provide direct access to the paranasal sinus, and through which a variety of medical treatments and medical procedures may be directed to the paranasal sinus. None of these surgical approaches has yet achieved wide-spread acceptance or success, and millions of chronic sinusitis patients continue to suffer long-term disability and discomfort.

SUMMARY OF INVENTION

Paranasal sinus access implant devices may be configured to be implanted in a human to provide fluid access to a paranasal sinus through an internal passage of such a paranasal sinus access implant device. Such paranasal sinus access implant devices have significant potential for performance of medical procedures and treatments of paranasal sinuses, but such potential has not yet been realized, and there is a continued need for implant devices and accompanying procedures that facilitate easy and effective implantation with good anchoring of the implant device, patient comfort, implant device durability post implantation and effective performance of medical procedures. Various aspects of this disclosure relate to paranasal sinus access implant devices, tools and methods for implantation procedures and treatments through implanted implant devices and kits including paranasal sinus access implant devices. For brevity, paranasal sinus access implant devices are sometimes referred to herein as simply implant devices.

A first aspect of the disclosure involves an implant device useful for implantation in a human to fluidly connect a lacrimal apparatus to a paranasal sinus through a fistula formed between the lacrimal apparatus and the paranasal sinus.

It has been found that implant devices may be better retained following implantation if the implant devices include anchoring surface features including protrusion areas and recess areas along a conduit that is to be inserted into the fistula for implantation. Anchoring is enhanced when a maximum outside diameter defined by protrusion areas to be disposed in the fistula is larger than the diameter of the fistula that was formed to accept the conduit of the implant device. This creates a snug fit of the conduit in the fistula, with tissue forcing itself into the recess areas of the anchoring surface feature. However, such implantation conduits made of relatively flexible plastic materials may bunch up, such as in the manner of an accordion, making it difficult to insert the conduit into the fistula for implantation. It has been found that by including a thicker conduit wall in a proximal portion of the conduit of an implant device than is included in a distal portion that is inserted first into the fistula, that the ease of insertion of the conduit may be significantly improved. In addition, a thicker conduit wall in a proximal portion of the conduit provides added mechanical durability of the conduit adjacent the proximal end of the implant device and reducing potential for mechanical damage to proximal portions of the conduit due to mechanical interactions that may occur between the implant device and tools used during an implantation procedure or during performance of medical treatments and other procedures following implantation.

The implant device of the first aspect may include:

a proximal end at a first longitudinal end of the device;

a distal end at a second longitudinal end of the device that is longitudinally opposite the first longitudinal end;

a conduit located between the proximal end and the distal end;

an internal passage through the conduit;

a length of the implant device longitudinally along the implant device between the proximal end and the distal end in a range of from 2 millimeters to 50 millimeters;

a width of the internal passage transverse to the length in a range of from 0.25 millimeter to 5 millimeters;

the conduit including a first longitudinal portion and a second longitudinal portion located toward the distal end relative to the first longitudinal portion;

the first longitudinal portion of the conduit having a minimum wall thickness (first minimum wall thickness) adjacent the internal passage; and the second longitudinal portion of the conduit having a minimum wall thickness (second minimum wall thickness) adjacent the internal passage that is smaller than the first minimum wall thickness;

the implant device configured to be implanted to fluidly connect the lacrimal apparatus to the paranasal sinus so that when implanted:

the proximal end is disposed in the lacrimal apparatus;

the distal end is disposed in the paranasal sinus; and the conduit is disposed through the fistula with at least a portion of each of the first longitudinal portion and the second longitudinal portion of the conduit disposed within the fistula and with at least a portion of the second longitudinal portion of the conduit disposed in the paranasal sinus.

A number of feature refinements and additional features are applicable to the first aspect of the disclosure. These feature refinements and additional features may be used individually or in any combination within the subject matter of the first aspect or any other aspect of the disclosure. As such, each of the following features may be, but are not required to be, used with any other feature or combination of features of the first aspect or any other aspect of the disclosure.

The first longitudinal portion of the conduit may or may not have a uniform wall thickness. The first longitudinal portion of the conduit may have a smooth exterior surface. The first longitudinal portion of the conduit may have a length of at least 3 millimeters, at least 4 millimeters, at least 5 millimeters, at least 8 millimeters or at least 10 millimeters. The first longitudinal portion of the conduit may often have a length that is no greater than 20 millimeters, no greater than 15 millimeters, no greater than 12 millimeters or no greater than 10 millimeters.

The first minimum wall thickness may be at least 0.25 millimeter, at least 0.3 millimeter, at least 0.35 millimeter or at least 0.4 millimeter. The first minimum wall thickness may often be no greater than 0.75 millimeter, no greater than 0.6 millimeter, no greater than 0.55 millimeter, no greater than 0.5 millimeter or no greater than 0.45 millimeter. The wall thickness of the first longitudinal portion of the conduit may be substantially the same and equal to the first minimum wall thickness over some portion of or the entire length of the first longitudinal portion.

The second longitudinal portion of the conduit may have a length of at least 3 millimeters, at least 4 millimeters, at least 5 millimeters, at least 8 millimeters or at least 10 millimeters. The second longitudinal portion of the conduit may often have a length that is no greater than 30 millimeters, no greater than 25 millimeters, no greater than 20 millimeters, no greater than 15 millimeters, no greater than 12 millimeters or no greater than 10 millimeters.

The second minimum wall thickness may be no greater than 0.6 millimeter, no greater than 0.5 millimeter, no greater than 0.45 millimeter, no greater than 0.4 millimeter, no greater than 0.35 millimeter, no greater than 0.3 millimeter, no greater than 0.25 millimeter or no greater than 0.2 millimeter. The second minimum wall thickness may often be at least 0.1 millimeter, at least 0.15 millimeter or at least 0.2 millimeter. The wall thickness of the second longitudinal portion of the conduit may be substantially the same over some portion or portions of the second longitudinal portion of the conduit. The second longitudinal portion of the conduit may have an exterior including an anchoring surface feature including protrusion areas and recess areas. The wall thickness at locations corresponding with the recess areas may be smaller than the wall thickness at locations corresponding with the protrusion areas. The second minimum wall thickness may occur at one or more locations corresponding with one or more of such recess areas.

The first minimum wall thickness may be at least 0.05 millimeter larger, at least 0.1 millimeter larger, at least 0.15 millimeter or at least 0.175 millimeter larger than the second minimum wall thickness. The first minimum wall thickness may be no more than 0.3 millimeter larger, no more than 0.25 millimeter larger or no more than 0.2 millimeter larger than the second minimum wall thickness.

The first longitudinal portion of the conduit may have a maximum exterior width (first maximum exterior width) that is smaller than a maximum exterior width of the second longitudinal portion of the conduit (second maximum exterior width). The second maximum exterior width may be at least 0.1 millimeter larger, at least 0.2 millimeter larger, at least 0.25 millimeter larger, at least 0.3 millimeter larger, at least 0.35 millimeter larger, at least 0.4 millimeter larger or at least 0.5 millimeter larger than the first maximum exterior width. The second maximum exterior width may often be no more than 1 millimeter, no more than 0.75 millimeter, no more than 0.5 millimeter or no more than 0.4 millimeter larger than the first maximum exterior width. The first maximum exterior width may be at least 1.25 millimeters, at least 1.5 millimeters, at least 1.75 millimeters or at least 2 millimeters. The first maximum exterior width may often be no greater than 3 millimeters, no greater than 2.5 millimeters, no greater than 2.25 millimeters or no greater than 2 millimeters. The second maximum exterior width may be at least 1.5 millimeters, at least 1.6 millimeters at least 1.75 millimeters, at least 2 millimeters, at least 2.25 millimeters or at least 2.5 millimeters. The second maximum exterior width may be no greater than 5 millimeters, no greater than 4 millimeters, no greater than 3 millimeters, no greater than 2.75 millimeters, no greater than 2.5 millimeters or no greater than 2.25 millimeters.

The first longitudinal portion of the conduit may have a minimum exterior width (first minimum exterior width) and the second longitudinal portion of the conduit may have a minimum exterior width (second minimum exterior width) that is smaller than the first maximum exterior width. The first minimum exterior width may be at least 0.1 millimeter larger, at least 0.2 millimeter larger, at least 0.25 millimeter larger, at least 0.3 millimeter larger, at least 0.35 millimeter larger, at least 0.4 millimeter larger or at least 0.5 millimeter larger than the second minimum exterior width. The first minimum exterior width may be no greater than 3 millimeters, no greater than 2.5 millimeters, no greater than 2.25 millimeters or no greater than 2 millimeters. The first minimum exterior width may be at least 1 millimeter, at least 1.25 millimeters, at least 1.5 millimeters, at least 1.75 millimeters or at least 2 millimeters. The first longitudinal portion of the conduit may have a substantially constant cross-section (e.g., constant circular cross-section), in which case the maximum and minimum exterior widths of the first longitudinal portion of the conduit are the same (e.g., diameter of constant circular cross-section). The second minimum exterior width may be no greater than 2.5 millimeters, no greater than 2 millimeters, no greater than 1.75 millimeters or no greater than 1.5 millimeters. The second minimum exterior width may often be at least 1 millimeter, at least 1.25 millimeter, at least 1.50 millimeters or at least 1.75 millimeters. The second longitudinal portion may have a surface geometry wherein the second minimum exterior width may be smaller than a second maximum exterior width of the second longitudinal portion. The second minimum exterior width may correspond with locations of the second minimum wall thickness.

The conduit may have a circular cross-section at some or all points along the length of the first and second longitudinal portions of the conduit. The first minimum wall thickness and the second minimum wall thickness may be tubular walls.

The conduit may be configured so that an exterior of the conduit comprises an anchoring surface feature that assists to anchor the implant device when the device is implanted. The anchoring surface feature includes protrusion areas and recess areas. The second minimum wall thickness may occur at a location corresponding with at least one of the recess areas. The implant device may be configured so that when implanted the conduit is disposed through the fistula with at least a portion of the recess areas disposed within the fistula and with at least a portion of the protrusion areas disposed in the fistula and engaging tissue exposed within the fistula to anchor the implant device. The structural and mechanical characteristics of protrusion occurrences in the protrusion areas may affect anchoring performance of the protrusion areas. The height of the protrusion areas relative to the recess areas may affect anchoring effectiveness when the implant device is implanted. A larger height may provide greater anchor effectiveness, but also may involve a larger overall width of the implant device that must be inserted into the fistula. The protrusion areas may have a height relative to the recess areas of at least 0.1 millimeter, at least 0.2 millimeter, at least 0.25 millimeter or at least 0.3 millimeter. The protrusions areas may have a height relative to the recess areas of no greater than 2 millimeters, no greater than 1.5 millimeter, no greater than 1 millimeter, no greater than 0.75 millimeter, no greater than 0.5 millimeter or no greater than 0.4 millimeter. The height may be of particular protrusion occurrences relative to adjacent areas of recesses. Protrusion occurrences are also referred to herein as anchor protrusions. Such anchor protrusions may be configured to flexibly deform when the conduit is inserted through the fistula for implantation, for example to flexibly deform in a direction opposite the direction of insertion when the anchor protrusions contact tissue disposed in the fistula during insertion. After insertion, the anchor protrusions may over time return to their original shape and extend deeper into adjacent tissue to better anchor the implant device. The mechanical properties of the anchor protrusions may be influenced by materials of construction. Preferred materials of construction for the protrusion areas, and also for the other portions of the implant device, are polymeric materials. The polymeric materials may preferably be medical grade materials. Some preferred polymeric materials are silicones and polyurethanes. For enhanced performance, the material of construction should have a rigidity that interacts positively with tissue in the vicinity of the fistula, for example to promote load sharing and good anchoring. One preferred material of construction is a polymeric material (e.g. silicone or polyurethane) having a durometer (Shore A) in a range having a lower limit of 50, 60, 70 or 80 and an upper limit of 100, 80, 70 or 60, provided that the upper limit must be larger than the lower limit. One preferred range is for a durometer (Shore A) of 60-100, with a range of 80-100 being even more preferred. For some implementations the polymeric material has a durometer (Shore A) of about 60, of about 80 or of about 100. Mechanical properties of the protrusion occurrences of the protrusion areas will also be affected by the geometry of the protrusion occurrences. The protrusion occurrences may have a width that tapers, or narrows, in a direction from a base toward a top of the protrusion occurrences, with the base being a portion of a protrusion occurrence disposed toward the internal passage of the conduit and a top of the protrusion occurrence being the extremity of the protrusion occurrence away from the internal passage of the conduit. The width may be transverse to the length of the conduit. The protrusion occurrences may have a width at the base that is no larger than 2 millimeters, no larger than 1.5 millimeters, no larger than 1.25 millimeters or no larger than 1 millimeter. One or more of the protrusion occurrences may have a width at the base that is at least 0.2 millimeter, at least 0.3 millimeter, at least 0.5 millimeter, at least 0.75 millimeter or at least 1 millimeter. The protrusion occurrences may have a width adjacent the top that is no larger than 0.75 times width at the base, no larger than 0.5 times the width at the base, or no larger than 0.25 times the width at the base. The protrusion occurrences may have a width midway between the base and the top that is no larger than 0.8 times the width of the base, no larger than 0.7 times the width of the base, no larger than 0.6 times the width of the base or no larger than 0.5 times the width at the base.

The protrusion areas may be provided by a single protrusion occurrence feature located to correspond with the interior of the fistula when the implant device is implanted. In more preferred implementations, the protrusion areas include multiple protrusion occurrences spaced on the exterior of the conduit. The protrusion occurrences may have a center-to-center spacing, in one or more directions, of at least 0.5 millimeter, at least 0.75 millimeter, at least 1 millimeter or at least 1.75 millimeters. The protrusion occurrences may have a center-to-center spacing of no greater than 2.5 millimeters, no greater than 2 millimeters or no greater than 1.75 millimeters. The protrusion occurrences may have a center-to-center spacing longitudinally along the conduit. The protrusion occurrences may have a center-to-center spacing that is at least 0.5 times the base width of the protrusion occurrences, or at least 1 times the base width of the protrusion occurrences or at least 2 times the base width of the protrusion occurrences. The protrusion occurrences may have a center-to-center spacing that is no more than 5 times a base width of the protrusion occurrences, no more than 3 times a base width of the protrusion occurrences or no more than 2 times a base width of the protrusion occurrences.

The protrusion areas may be located on a longitudinal portion of the conduit that includes at least a portion of the conduit that will be disposed within a fistula when the implant device is implanted. The protrusion areas may be on a longitudinal portion of the conduit that extends for at least 2 millimeters along the length of the implant device, that extends for at least 3 millimeters along the length of the implant device, that extends for at least 4 millimeters along the length of the implant device, that extends for at least 5 millimeters along the length of the implant device or that extends for at least 8 millimeters along the length of the implant device. A longitudinal portion of the conduit including the protrusion areas may be no longer than 20 millimeters, no longer than 15 millimeters or no longer than 10 millimeters. A longitudinal portion of the conduit including the protrusion areas may be disposed at least 2 millimeters from the proximal end of the device, at least 3 millimeters from the proximal end of the device, or at least 4 millimeters from the proximal end of the device. When the implant device has a head, a longitudinal portion of the conduit including the protrusions may be disposed at least 1 millimeter, at least 2 millimeters or at least 3 millimeters from the head. Providing significant distance between the head and commencement of the protrusion areas permits the head to better "float" on the surface of tissue, which may enhance patient comfort and device performance. The protrusion areas may be disposed along a longitudinal portion of the conduit with the protrusion areas covering no more than 35% of the area along that longitudinal portion of the conduit, no more than 25% of the area along that longitudinal portion of the conduit or not more than 20% of the area along that longitudinal portion of the conduit. Providing significant spacing between protrusion occurrences may permit better engagement of tissue by the anchoring surface feature. Some or all of the protrusion occurrences may be on the second longitudinal portion of the conduit.

The protrusion areas may comprise at least one circumferential ridge. By circumferential ridge is meant a ridge that extends around an entire circumference of the conduit. The protrusion area may comprise at least two, at least three or at least five circumferential ridges. The protrusion areas may comprise a spiral ridge. Such a spiral ridge may extend along a longitudinal portion of the conduit. The protrusion areas may comprise a knob or may comprise multiple knobs. The anchoring surface feature may comprise a textured surface, with the protrusion areas comprising protruding portions of the textured surface and the recess areas comprising recess portions of the textured surface.

The length of the implant device may be selected to provide sufficient conduit length for extending through the entire length of the fistula plus any extension distance desired in the lacrimal apparatus proximal to the fistula and in the paranasal sinus distal to the fistula. The length of the implant device and/or of the conduit may be in a range having a lower limit of 2 millimeters, 3 millimeters, 4 millimeters, 5 millimeters, 8 millimeters, 10 millimeters or 12 millimeters and an upper limit of 50 millimeters, 40 millimeters, 30 millimeters, 25 millimeters, 20 millimeters, 15 millimeters or 10 millimeters, provided that the upper limit is larger than the lower limit. One preferred range for some implementations when the fistula is between the orbit and the ethmoid sinus or the maxillary sinus is for the length of the implant device and/or for the length of the conduit to be in a range of from 10 millimeters to 30 millimeters, with a range of from 15 millimeters to 25 millimeters being more preferred. By length of the implant device or conduit it is meant the dimension longitudinally along the implant device or the conduit, as the case may be, from the proximal end to the distal end of the implant device or conduit, and may be along a longitudinal axis through the internal passage. The length may be a straight line, for example when the internal passage is straight, or the length may be curvilinear or some other shape, for example when the internal passage is not linear. When a reference is made herein to transverse to the length, the reference is to a right angle to the longitudinal direction of the length at that point (e.g., right angle to a line of the length or to a line tangent to a curve of the length).

The implant device may advantageously be designed with a conduit of appropriate width dimensions to fit snuggly within a desired size of fistula. The implant device may have a first exterior width dimension defined by a maximum extent of the protrusion areas transverse to the length of the device, with the first exterior width being within a range having a lower limit of 0.75 millimeter, 1 millimeter, 1.25 millimeters, 1.5 millimeters, 1.75 millimeters or 2 millimeters and an upper limit of 8 millimeters, 7 millimeters, 6 millimeters, 5 millimeters, 4 millimeters, 3 millimeters, 2 millimeters or 1.75 millimeters, provided of course that the upper limit must be larger than the lower limit. The conduit may have a second width dimension defined by the minimum extent of the recess areas transverse to the length of the device, and which second exterior width dimension will be smaller than the first exterior width dimension defined by the protrusion areas. The second exterior width dimension defined by the recess areas may be smaller than the exterior width dimension defined by the protrusion areas by an amount within a range having a lower limit of 0.2 millimeter, 0.25 millimeter, 0.35 millimeter or 0.5 millimeter and having an upper limit of 1.5 millimeters, 1 millimeter or 0.75 millimeter. The height of the protrusion areas may be one-half the difference between the first exterior width and the second exterior width. Either one of or each one of the first exterior width and the second exterior width may be the diameter of a circle.

The implant device may include one or a plurality of side openings through the conduit wall of a distal portion of the conduit, which distal portion may be or include a portion of the conduit that is designed to be disposed within a paranasal sinus when the implant device is implanted to provide fluid access through the implant device to the paranasal sinus. The side openings may be open into the internal passage through the conduit and may provide a passage for fluid communication between the internal passage of the implant device and the paranasal sinus even if the distal opening of the internal passage at the distal end of the conduit were to become blocked or restricted for some reason. One or more of the side openings may be through a wall of the second longitudinal portion of the conduit, and may be though a wall having the second minimum wall thickness. One or more of the side openings may be located within one or more recess areas of an anchoring surface feature of the conduit (e.g., between circumferential ridges). With a thinner minimum wall thickness in the second longitudinal portion of the conduit than the first longitudinal portion of the conduit, the second longitudinal portion of the conduit, and in particular near a distal end of the second longitudinal portion of the conduit, may be more prone to restriction due to collapse of the conduit at or near the distal end, and the side openings 850 provide an alternative fluid access to the paranasal sinus.

The implant device may include a head adjacent to the conduit at the proximal end of the implant device. The implant device may be configured so that when the implant device is implanted, the head is disposed in the lacrimal apparatus, and preferably with the head located in the orbit. The head may beneficially keep the implant device from migrating through the fistula toward the paranasal sinus following implantation of the implant device. The head may comprise a flanged tissue engagement surface on a side of the head disposed toward the conduit and configured to engage tissue outside of and adjacent to the fistula when the implant device is implanted. The flanged tissue engagement surface may be a flat surface. The flanged tissue engagement surface may have non-flat surface features configured to improve seating of the surface against tissue, such as for example to inhibit rotation of the implant device within the fistula after implantation. The head may have a face surface opposite the flanged tissue engagement surface and also disposed away from the conduit and disposed away from tissue engaged by the flanged tissue engagement surface when the implant device is implanted. The face surface may be substantially flat. The face surface may be disposed at the proximal end of the implant device and the internal passage may open at the face surface. The separation distance between the face surface and the flanged tissue engagement surface may be in a range having a lower limit of 0.25 millimeter, 0.5 millimeter or 0.75 millimeter and having an upper limit of 2 millimeters, 1.5 millimeters or 1 millimeter. Such separation distance need not be constant across the flanged tissue engagement surface and face surface. A maximum separation distance between the face surface and the flanged tissue engagement surface may be referred to as the depth of the head, and such depth may be in a range described above for the separation distance between the face surface and the flanged tissue engagement surface. The flanged tissue engagement surface need not be continuous and may be divided into multiple distinct surface portions. For example, the flanged tissue engagement surface may include a first flanged portion disposed to one side of the internal passage and a second flanged surface portion disposed to a second side of the internal passage that is opposite the first side. Each of the face surface and the flanged tissue engagement surface may have a length dimension that represents a maximum separation distance between points on an outer edge of the respective surface, and may each have a width dimension that is a maximum separation distance between points on the outer edge transverse to the length dimension. The length dimensions of the face surface and the flanged tissue engagement surface may be the same or may be different. The width dimensions of the face surface and the flanged tissue engagement surface may be the same or may be different. The face surface and the flanged tissue engagement surface may have corresponding outer edges. The length dimension of any or all of the face surface, the flanged tissue engagement surface and the head may be larger than a first exterior width of the conduit defined by an extent of the protrusion areas transverse to the length of the implant device, when the implant device includes an anchoring surface feature such as summarized above. The length dimension of any or all of the face surface, the tissue engagement surface and the head may be in a range having a lower limit of 1 millimeter, 2 millimeters, 3 millimeters, 4 millimeters or 5 millimeters and an upper limit of, 10 millimeters, 8 millimeters or 7 millimeters. The width dimension of any or all of the face surface, tissue engagement surface and the head may be in a range having a lower limit of 0.5 millimeter, 1 millimeter, 1.5 millimeters or 2 millimeters and an upper limit of 5 millimeters, 4 millimeters or 3 millimeters. The length dimension of any or all of the face surface, the flanged tissue engagement surface and the head may be at least 1 millimeter, at least 2 millimeters, at least 3 millimeters or at least 4 millimeters larger than such first exterior width of the conduit defined by an extent of the protrusion areas, when the implant device includes an anchoring surface feature such as summarized above. A ratio of the length of any of or all the face surface, the flanged tissue engagement surface and the head to such a first exterior width of the conduit may be at least 2. Such a ratio may be smaller than 4. The width of any or all of the face surface, the flanged tissue engagement surface and the head may be not larger than, or may be smaller than (e.g., by at least 0.1 mm or by at least 0.2 mm), such a first exterior width of the conduit defined by an extent of the protrusion areas, when the implant device includes an anchoring surface feature such as summarized above. A ratio of the length dimension to the width dimension for any or all of the face surface, the flanged tissue engagement surface and the head may be in a range having a lower limit of 1, 1.5, 2 or 2.5 and an upper limit of 5, 4, 3 or 2.5, provided of course that the upper limit must be larger than the lower limit. Having a larger length dimension to width dimension on the head is particularly preferred when the head will be located in the orbit between the lacrimal caruncle and the plica semilunaris, because the length dimension may advantageously align in a vertical direction next to the eyeball and will help provide sufficient flanged surface area to effectively anchor the implant device on the proximal end and impede conjunctival tissue from covering the opening into the internal passage of the implant device, compensating for the narrower width. This is particularly advantageous when using polymeric materials of construction as described above.

The internal passage through the implant device may have a substantially uniform shape along the entire length of the implant device, or may have a varying shape. The internal passage may be substantially straight from the proximal end of the device to the distal end of the device. The internal passage may have a cross-section available for flow (transverse to the length of the device) that is substantially uniform from the proximal end to the distal end of the implant device. The internal passage may have a substantially circular cross-section. The internal passage may have a substantially elliptical cross-section. The width of the conduit (maximum dimension across the cross-section of the internal passage available for flow) may be in a range having a lower limit of 0.25 millimeter, 0.5 millimeter or 0.75 millimeter and 1 millimeter and an upper limit of 5 millimeters, or 4 millimeters or 3 millimeters, 2 millimeters or 1.5 millimeters.

The lacrimal apparatus and a paranasal sinus may be in fluid communication through the internal passage of the implant device when the implant device is implanted. The conduit may extend from adjacent the proximal end of the implant device. The conduit may extend to adjacent the distal end of the implant device. The internal passage may have a first end open at the proximal end and a second end open at the distal end, and when the implant device is implanted the first end of the internal passage may open in the lacrimal apparatus and the second end of the internal passage opens in the paranasal sinus The implant device may be configured for implantation with the conduit passing through a fistula between a location in a lacrimal apparatus within the orbit and a paranasal sinus selected from the group consisting of a frontal sinus, an ethmoid sinus, a maxillary sinus and a sphenoid sinus, with a frontal sinus, a maxillary sinus or an ethmoid sinus being preferred, with an ethmoid sinus or a maxillary sinus being more preferred, and with an ethmoid sinus being particularly preferred. The implant device may be configured for implantation with the conduit passing through a fistula between a location in the lacrimal apparatus within the nasolacrimal duct and a paranasal sinus selected from the group consisting of an ethmoid sinus and a maxillary sinus. The location within the nasolacrimal duct may be within the lacrimal sac.

The implant device is primarily configured for and described herein with primary reference to the implant device being implantable in a fistula that may be formed between the lacrimal apparatus and a paranasal sinus to provide a passage from the lacrimal apparatus to the paranasal sinus. The implant device is also implantable in a fistula that may be formed between the lacrimal apparatus (e.g., from the corner of medial portion of the orbit between the lacrimal caruncle and the plica semilunaris) and the nasal cavity, for example for enhanced drainage of lacrimal fluid, and such applications directed to the nasal cavity are within the scope of the different aspects of the disclosure.

A second aspect of the disclosure involves an implantation kit with components for implantation of an implant device to provide an artificial fluid path in fluid communication with the lacrimal apparatus. A kit of the second aspect may include a paranasal sinus access implant device and at least one additional component useful in connection with implantation of the implant device or performance of a medical treatment or procedure through the implant device.

A number of feature refinements and additional features are applicable to the second aspect of the disclosure. These feature refinements and additional features may be used individually or in any combination within the subject matter of the second aspect or any other aspect of the disclosure. As such, each of the following features may be, but are not required to be, used within any other feature or combination of features of the first aspect, the second aspect or any other aspect of the disclosure.

The implant device may comprise:
a proximal end and a distal end at opposite longitudinal ends of the implant device;
a conduit located between the proximal end and the distal end;
an internal passage extending through the conduit;
a longitudinal length between the proximal end and the distal end of the implant device in a range of from 2 millimeters to 50 millimeters;
a width of the internal passage transverse to the length in a range of from 0.25 millimeter to 5 millimeters; and
the implant device being configured to be implanted with the proximal end of the implant device disposed in the lacrimal apparatus and at least a portion of the conduit disposed in a fistula opening into the lacrimal apparatus.

The implant device may be an implant device of the first aspect of the disclosure or may have any feature or combination of features described for the first aspect of the disclosure, for example even if the implant device is not according to the first aspect.

A kit may include any, or any combination of any, apparatuses, tools, devices, products, components or treatment compositions described herein.

A kit may include a fluid treatment composition deliverable to a paranasal sinus through the implant device following implantation of the implant device to provide fluid access to the paranasal sinus. Such a fluid treatment composition may be suitable for being conducted to the internal passage of an implant device through manipulation of a fluid dispenser for delivery to a paranasal sinus, for example to treat for sinusitis or some other condition of the paranasal sinus. The treatment composition may be an aqueous irrigation liquid. The treatment composition may be a drug treatment composition. The drug treatment composition may comprise at least one drug for treating sinusitis or other condition of a paranasal sinus. The drug treatment composition may comprise one or more of the following: an antibiotic, a steroid, an anti-viral, an antihistamine, an anti-fungal, a mast cell stabilizer, a mucolytic, a non-steroidal anti-inflammatory drug (NSAID), a vasoconstrictor and an immunosuppressant. Some example antibiotics include: sulfa, or sulfonamide, drugs, such as for example sulfacetamide (e.g., in OCUSOL) and sulfisoxazole (e.g., in GANTRISIN®); macrolide drugs, such as for example azithromycin (e.g., in AZACITE®) and erythromycin (e.g., in ERYPED®); aminoglycoside drugs, such as for example tobramycin (e.g., in TOBREX®) and gentamicin (e.g., in GENOPTIC®); fluoroquinolone drugs, such as for example ciprofloxacin (e.g., in CILOXAN®), besifloxacin (e.g., in BESIVANCE®) and moxifloxacin (e.g., in VIGAMOX®); tetracycline drugs, such as for example oxytetracycline (e.g., in CODEX); and antibiotic drug combinations, such as for example containing a combination of bacitracin, neomycin and polymyxin B (e.g., in OCUSPORE B) and a combination of gramicidin, neomycin and polymyxin B (e.g., in NEOCIN PG). Some example antivirals include gancyclovir (e.g., in ZIRGAN®) and trifluridine (e.g., in VIROPTIC®). Some example steroids include loteprednol (e.g., in LOTEMAX®) and prednisolone (e.g., in PRED FORTE®). Some example anthistimines include ketotifen (e.g., in ALAWAY®), otopatadine (e.g., in PATADAY®) and pinastine (e.g., in ELESTAT®).

Some example mast cell stabilizers include nedocromil sodium (e.g., in ALOCRIL®) and lodoxamide (e.g., in ALOMIDE®). Some example anti-fungals include natamycin (e.g., in NATACYN®) and euconzol. Some example mucolytics include N-acetylcysteine (e.g., in PARVOLEX). Some example NSAID materials include nepafenac (e.g., in NEVANAC®) and bromfenac (e.g., in BROMDAY®). Some example vasoconstrictors include naphazoline (e.g., in NAPHCON A®) and tetrahydrozoline (e.g., in VISENE®). Some example immunosuppressants include cyclosporine (e.g., in RESTASIS®). All of the aforementioned materials include any pharmaceutically acceptable salts thereof.

The fluid treatment composition may be disposed within a fluid container as provided in the kit. The fluid container may contain any desired volume of the treatment composition. Such a volume may be in a range having a lower limit of 0.1, 0.25, 0.5, 0.75 or 1 milliliter and an upper limit of 5, 3 or 2 milliliters. Such a range may be the total treatment composition contained within the fluid container or may be the volume of treatment composition contained within the fluid container that is deliverable from the fluid container, which may be referred to as the deliverable volume. The deliverable volume refers to that volume of fluid in the fluid container that can be effectively delivered from a fluid dispenser. The delivery volume may be less than the total volume of treatment composition contained in the fluid container because of residual treatment composition that may be retained in the fluid container or within the fluid dispenser, for example residual treatment composition that may be adhered on internal wall surfaces of (e.g., internal wall surfaces of the fluid container, for example internal wall surfaces of a syringe barrel) or that remain in fluid conduction portions of such a fluid dispenser between the fluid container and a distal fluid ejection tip (e.g., remaining fluid in a dispensing needle).

The fluid container that contains the treatment composition may be part of a fluid dispenser. The fluid dispenser may be manipulable to dispense at least a portion of the treatment composition from the fluid container into the internal passage or through the internal passage directly into a paranasal sinus following implantation of the implant device. The fluid container may be provided in the kit by a syringe, which may be or be part of such a fluid dispenser. The fluid container may include at least a portion of a syringe barrel. A fluid dispenser may include a fluid ejection member in fluid communication with the treatment composition in the fluid container. Such a fluid ejection member may be insertable in the internal passage of the implant device, and the fluid dispenser may be manipulable when the fluid ejection member is inserted in the internal passage of the implant device when the implant device is implanted to eject at least a portion of the treatment composition from a distal end of the fluid ejection member into the internal passage of the implant device or distal of the distal internal passage directly into a paranasal sinus. For example, a distal fluid ejection tip of the fluid ejection member may be disposed in the internal passage and the treatment composition may be dispensed into the internal passage to then flow into the paranasal sinus, or the fluid ejection member may be inserted through the internal passage until the distal tip is disposed in the paranasal sinus distal of a distal end of the internal passage, and the treatment composition may be dispensed directly into the paranasal sinus. The fluid ejection member may be connected with a syringe, such as through a leur connection. The fluid ejection member may have an insertion portion configured to be inserted into the internal passage and such an insertion portion may have a maximum outside width (e.g., diameter) of no larger than 1.75 millimeters, no larger than 1.5 millimeters, no larger than 1.25 millimeters, no larger than 1 millimeter or no larger than 0.9 millimeter. The fluid ejection member may be or include a hollow needle having a blunt tip (e.g., blunt tip hypodermic needle). The fluid ejection member may be covered with a removable protective cap. For example, the kit may include a pre-filled syringe containing the treatment composition and fitted with a hypodermic needle that is covered with a protective cap that that protects the needle prior to use. A kit may include multiple different treatment compositions, and may include multiple fluid containers (e.g., multiple syringes) each containing a different treatment composition.

Forming a fistula for implantation of an implant device to provide a fluid passage between the lacrimal apparatus and a paranasal sinus involves making a hole through a wall of the bone in which the cavity of the paranasal sinus is located. As described herein, such a hole may be made by a sytlet or other solid piercing instrument and then widened as needed to form the fistula to the desired size for implantation of the implant device. For example following the initial piercing to make an initial hole, the hole may be dilated using dilators to make the hole progressively larger until the desired size is obtained. However, it has been found that when forming a fistula for implantation in such a manner, the bone tends to crack and shatter in the vicinity of hole. Although this does not present a medical problem, it has been found that if the bone is kept more in-tact in the vicinity of the hole, then the bone may provide mechanical support to help secure the implant device in place and prevent the implant device from migrating out of the fistula following implantation. Bone integrity in the vicinity of the fistula may be improved by cutting the hole for the fistula rather than piercing and dilating the hole. By cutting through the bone, rather than pushing through the bone, the bone remains more in-tact in the vicinity of the hole and provides better mechanical support to help retain the implant device in place in the fistula following implantation. The implantation kit of the second aspect may include tools useful for cutting a hole for a fistula and implanting an implant device.

A kit may include at least one cutting tool for cutting away tissue to form a fistula through which the implant device may be implanted during an implant procedure. Such a cutting tool may include a hollow member having a hollow cutting tip at a distal end of the cutting member configured to cut tissue to size the fistula for implantation of the implant device through the fistula. Such a cutting member may have a cutting width that is smaller than a maximum exterior width of a conduit of the implant device configured to be disposed through the fistula during implantation. Such a cutting tool may be a drill.

A kit may include a cutting tool that may be guidable by a guide member disposable through an internal passage of the cutting tool. The cutting tool may include a hollow cutting member that has a hollow cutting tip at a distal end of the cutting member configured to cut tissue to size the fistula for implantation of the implant device through the fistula. The hollow cutting tip of the cutting tool may be configured to make a larger diameter cut to enlarge a smaller-diameter preliminary cut that may have been previously made to accommodate the guide member, or the cutting tool may be configured to make a desired final cut without prior formation of a smaller initial fistula. The cutting member may be configured to be slidably engaged with the guide member with the guide member disposed through a passage in the cutting member with the distal end of the guide member disposed distal of the distal end of the cutting member. A distal end of the guide member may be configured to be disposed in or distal of the fistula such that the cutting member is slidable over the guide member, for example to conduct the cutting tip of the cutting member to cut tissue to size the fistula for implantation of the implant device when a smaller initial fistula has already been formed or to permit retraction of the cutting member while leaving the guide member in place for use to conduct another tool or tools to the location of the fistula, for example an implantation tool for inserting an implant device into the fistula in position for implantation following cutting a fistula of a desired size for implantation.

A cutting member of a cutting tool may be or include a hollow needle or a cutting cannula. The cutting member may have a cutting width, or diameter in the case of a circular cut, that is smaller than a maximum exterior width of the conduit of the implant device. The maximum exterior width of the conduit of the implant device may occur at one or more protrusion areas that form part of an anchoring surface feature on the conduit. The cutting width may be at least 0.1 millimeter smaller, at least 0.2 millimeter smaller, at least 0.25 millimeter smaller, at least 0.3 millimeter smaller, at least 0.35 millimeter smaller or at least 0.4 millimeter smaller than the maximum exterior width of the conduit of the implant device. The cutting width may be not more than 1 millimeter, 0.75 millimeter, 0.6 millimeter, or 0.5 millimeter smaller than the maximum exterior width of the conduit. The cutting width may be not larger than 5 millimeters, 4 millimeters, 3.5 millimeters, 3 millimeters, 2.5 millimeters, 2.25 millimeters, 2 millimeters, 1.9 millimeters or 1.8 millimeters. The cutting width may be at least 1 millimeter, 1.5 millimeter, 1.75 millimeter or 1.85 millimeter.

A kit may include an implantation guide tool with a proximal end and a distal end and including a guide member extending longitudinally in a direction from the proximal end toward the distal end of the implantation guide tool. The guide member and internal passage may be configured for mounting the implant device on the guide member with the guide member disposed through the internal passage of the implant device with a distal end of the guide member disposed distal of the distal end of the implant device, and the distal end of the guide member may be configured to be disposed in or distal of the fistula such that the implant device mounted on the guide member is slidable on the guide member toward the distal end of the guide member to conduct the implant device into the fistula for implantation. The guide member may be configured for insertion through a passage through a tool (e.g., cutting tool or carrier tool) to guide the tool to the site of a fistula.

In one example of a guide member, the guide member may be a guide wire or a small diameter needle (e.g., 20 gauge spinal needle), a cutting member may be a larger gauge needle through which the guide member may be inserted (e.g., 12 to 14 gauge spinal needle), and an implant device may have an internal passage through which the guide member may be inserted (e.g., 1 mm).

The guide member may be any appropriately sized member on which the implant device or a tool to be guided by the guide member may be slidably conducted along the guide member for implantation. The guide member may be a rigid, flexible or malleable material. The guide member may be a solid member, for example a solid guide wire or a stylet. The guide member may be a hollow member, for example the guide member may be or include a needle or cannula. The guide member may include a cutting end at the distal end configured to cut tissue to form at least a portion of the fistula. Such a hollow guide member with a cutting end may be a needle or cutting cannula. Such a hollow guide member with a cutting end may be useful to cut an initial hole that may then be made larger to a desired size for implantation of the implant device.

A kit may include a carrier tool, also referred to as an implantation tool, for carrying the implant device during an implantation procedure. Such a carrier tool may include a carrier member with a distal tip, with the carrier member being adapted to be disposed through a fistula between the lacrimal apparatus in the orbit and a paranasal cavity with the distal tip located in the paranasal cavity. The carrier tool may include a hand-manipulable handle connected to the carrier member. An implant device may be mountable on the carrier member for implantation of the implant device, with the mounted implant device disposed between the handle and the distal tip with the carrier member disposed through the internal passage and with a proximal end of the implant device disposed toward the handle and a distal end of the implant device disposed toward the distal tip of the member. When the implant device is mounted for implantation, the carrier member, and the carrier tool, may be disengageable from the implant device for implantation of the implant device during an implantation procedure to provide fluid access to a paranasal sinus. A clearance fit of the carrier member in the internal passage of the implant device when the implant device is mounted on the carrier member for implant placement may be small to ensure a close fit and help prevent lateral deformation of the implant device during implantation. For example such a clearance fit may be no larger than 0.5 millimeter, no larger than 0.4 millimeter, no larger than 0.3 millimeter, no larger than 0.2 millimeter or no larger than 0.1 millimeter. Having a close fit between of the carrier member in the internal passage of the implant device helps prevent accordion-like bunching of the implant device during an implant procedure as the carrier tool with the mounted device may be advanced to advance (push) the carrier member and the mounted implant device into the fistula for implantation.

Any and all parts of a kit may conveniently be contained within a common package, such as a common box, bag or other common packaging enclosure. Some or all components of a kit may be sterilized and sealed within hermetically sealed enclosures, such as for example hermetically sealed bags or wrapping.

A third aspect of the disclosure involves a method for performing a medical procedure in relation to a paranasal sinus and/or administering a treatment composition or performing a medical operation through an implanted implant device directed to the paranasal sinus.

A number of feature refinements and additional features are applicable to the third aspect of the disclosure. These feature refinements and additional features may be used individually or in any combination within the subject matter of the third aspect or any other aspect of the disclosure. As such, each of the following features may be, but are not required to be, used within any other feature or combination of features of the first aspect, the second, the third aspect or any other aspect of the disclosure.

A medical procedure of the method of a third aspect may include implanting an implant device to provide an artificial fluid path in fluid communication with the lacrimal apparatus. The method of the third aspect may involve cutting away tissue to form a fistula for implantation of an implant device, which is particularly advantageous when the fistula is to pass through bone, such as in the case of implant devices designed to provide an artificial fluid passage between the lacrimal apparatus and a paranasal sinus. The cutting away tissue may be to form a fistula of a size to receive at least a portion of a conduit of an implant device, the fistula having a proximal end opening into the lacrimal apparatus, and implanting the implant device with at least a portion of the conduit of the implant device in the fistula. Following the cutting away tissue, the method may include implanting an implant device to fluidly connect the lacrimal apparatus and the paranasal sinus. The implanting may include advancing the implant device into an implantation position using a carrier tool. The implanting may include advancing the carrier tool to have the carrier tool push the implant device into an implant position. The implanting may include sliding the implant device along a guide member or along a carrier member of a carrier tool into an implantation position. The implanting may include disengaging the carrier tool from the implant device positioned in the implant position.

In one variation, a method of the third aspect may comprise:

cutting away tissue to form a fistula having a proximal end opening into the lacrimal apparatus and a distal end opening into a paranasal sinus;

implanting an implant device to fluidly connect the lacrimal apparatus and the paranasal sinus, the implanting comprising:

advancing a carrier tool on which the implant device is mounted to push the conduit into the fistula from the proximal end of the fistula until the implant device is in an implantation position with a distal end of the conduit disposed in the paranasal sinus; and disengaging the carrier tool from the implant device positioned in the implantation position.

In another variation, a method of the third aspect may comprise:

cutting away tissue to form a fistula of a size to receive at least a portion of a conduit of an implant device, the fistula having a proximal end opening into the lacrimal apparatus;

with a guide member having a distal end disposed in or distal of the fistula, sliding the implant device along the guide member toward the fistula; and disposing at least a portion of the conduit of the implant device in the fistula.

A method procedure of the method of the third aspect may be or involve administering a treatment composition to a paranasal sinus through an implant device that fluidly connects the lacrimal apparatus with the paranasal sinus.

A method of the third aspect, or a portion thereof may be performed using a kit of the second aspect of this disclosure or parts of such a kit. When the method includes cutting away tissue, the cutting away tissue may comprise cutting the tissue with a cutting tool of such a kit. During the cutting away or some portion thereof, the cutting member may or may not be disposed over and conducted to the location for the cut by the guide member. For example, a preliminary cut may be made for form a preliminary hole of a smaller size, the guide member may be disposed with a distal end in or distal to the preliminary hole, and the cutting member may be slid over the guide member to cut tissue to produce a larger fistula of the desired size for implantation of the implant device. As another example, a single final cut may be made to make a hole of a final desired size for implantation which may be made without the aid of a guide member and without making a preliminary hole. In that regard, a shoulder on the ethmoid bone facing the orbit has been identified that is a convenient landmark for orienting a cut into the ethmoid sinus. The shoulder has been named the shoulder of Willoughby. When the method includes administering a treatment composition to a paranasal sinus the treatment composition may be as described in relation to the kit of the second aspect.

Cutting away tissue may be accomplished by removing tissue by drilling through the tissue with a drill, which drill may be provided in a kit of the second aspect.

The implant device for the third aspect (or for the second aspect) may include:

a proximal end and a distal end at opposite longitudinal ends of the implant device;

the conduit located between the proximal end and the distal end;

a first internal passage extending between the proximal end and the distal end of implant device and through the conduit, the first internal passage having a first end open at the proximal end of the implant device and a second end open at the distal end of the implant device;

a longitudinal length between the proximal end and the distal end of the implant device in a range of from 2 millimeters to 50 millimeters;

a width of the first internal passage transverse to the length in a range of from 0.25 millimeter to 5 millimeters; and the implant device being configured to be implanted with the proximal end of the implant device disposed in the lacrimal apparatus.

The implant device for the third aspect may be an implant device of the first aspect of the disclosure or may include any feature or features described with respect to the first aspect of the disclosure, for example even if the implant device is not according to the first aspect. The implant device may as described with respect to the second aspect or may have any feature or features described in relation to the second aspect.

These and other aspects, and features thereof, are further described or will be apparent from the drawings and the description provided below.

BRIEF DESCRIPTION OF THE DRAWINGS

The drawings are included to aid in the understanding of various aspects of the disclosure and possible feature refinements and additional features applicable thereto. Features shown in the drawings are presented for purposes of illustration only, and are not necessarily to scale and are not necessarily detailed in every respect.

FIG. 9 is an illustration of various head configurations for an implant device.

DETAILED DESCRIPTION

Figure 1:
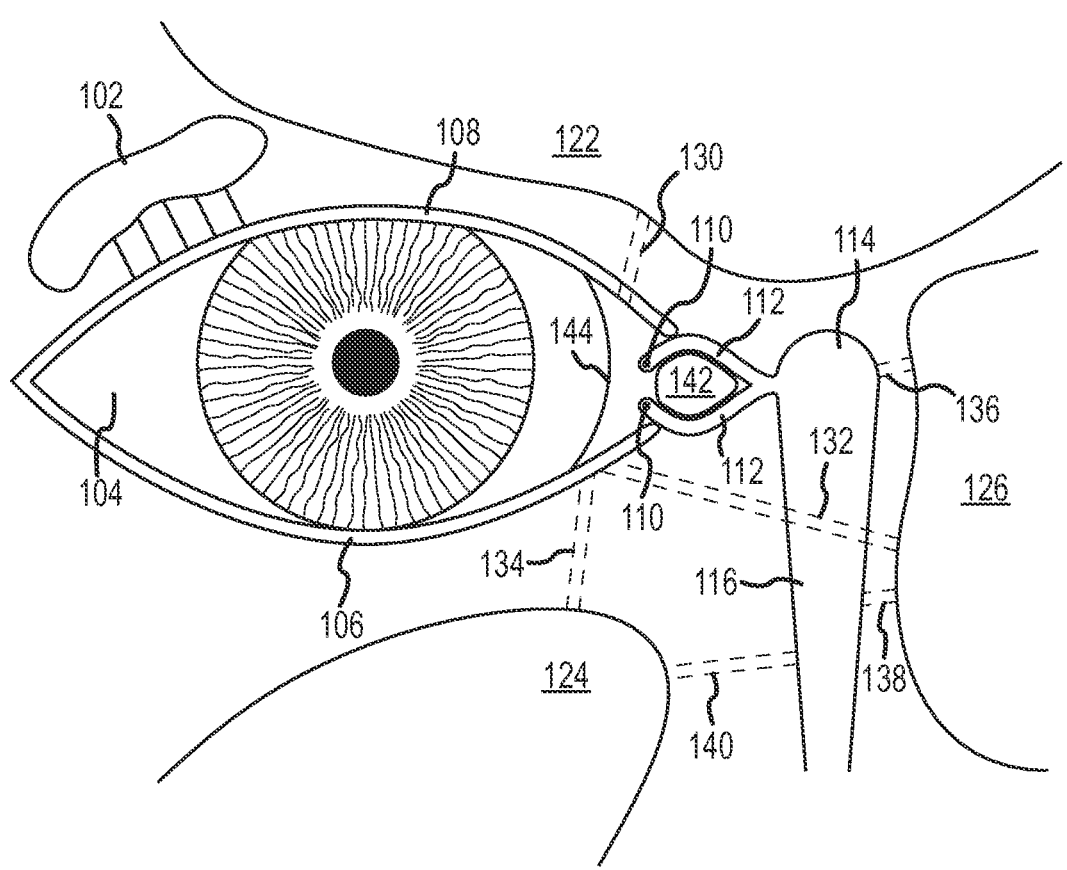
FIG. 1 is an illustration showing some example routes for an implant to provide fluid access from the lacrimal apparatus to a paranasal sinus.
Figure 2:
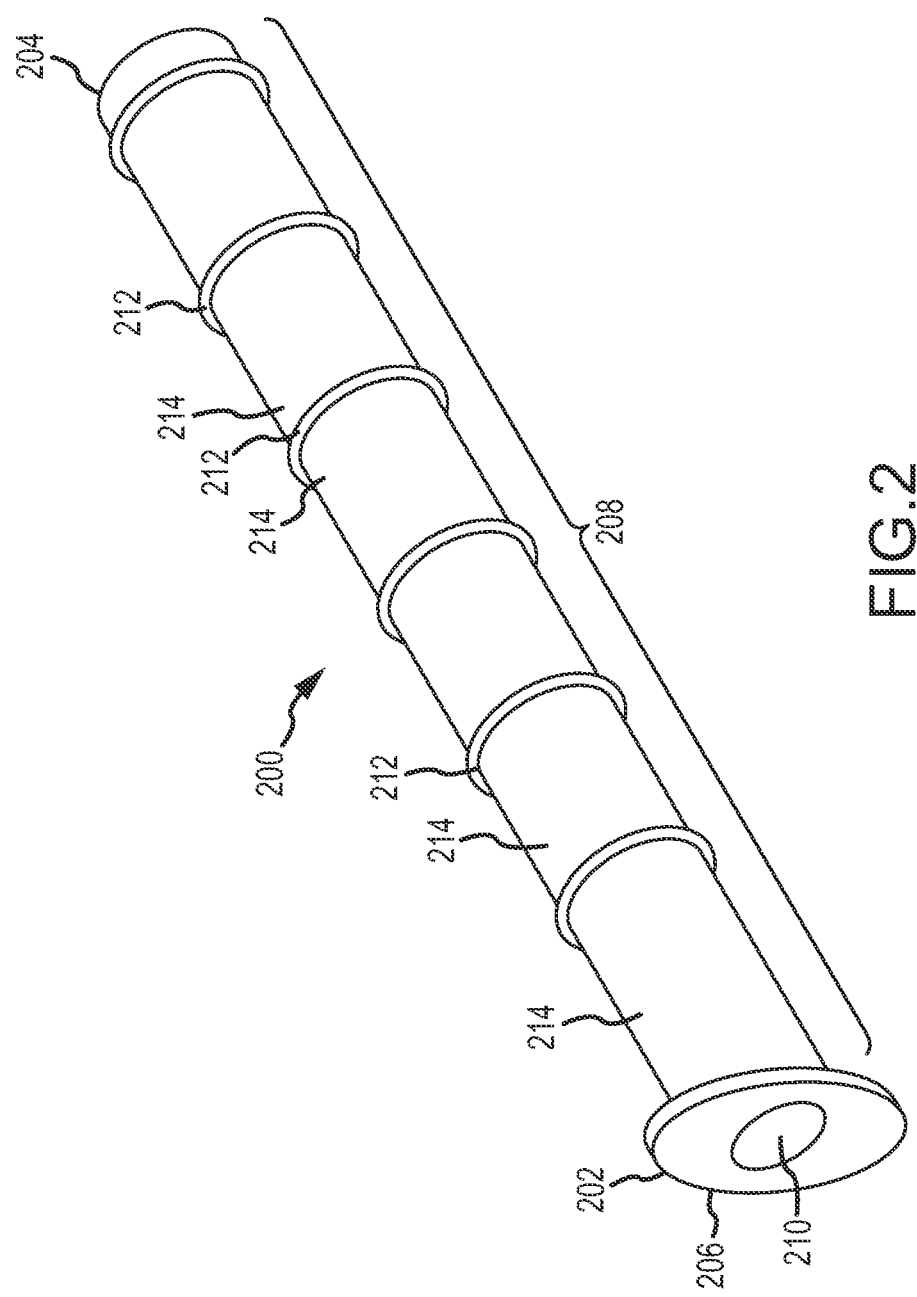
FIG. 2 is perspective view of one embodiment of an implant device.
Figure 3:
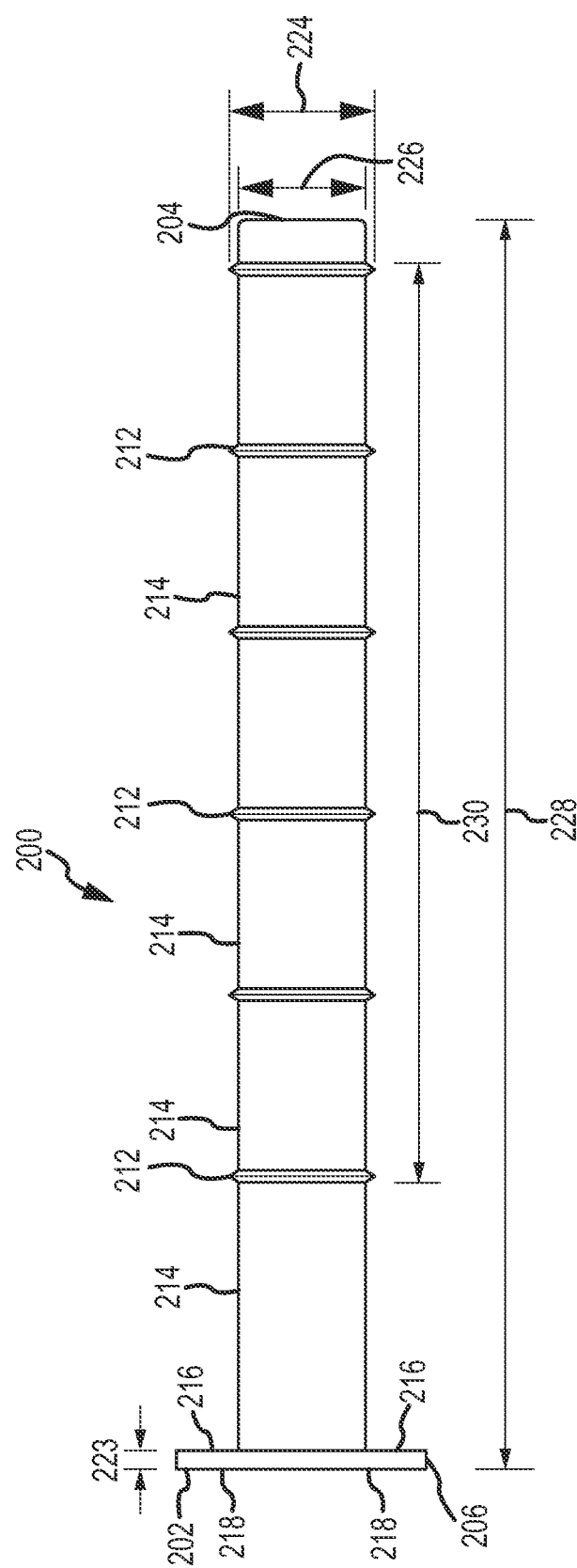
FIG. 3 is a side view of the same embodiment of an implant device as shown in FIG. 2.
Figure 4:
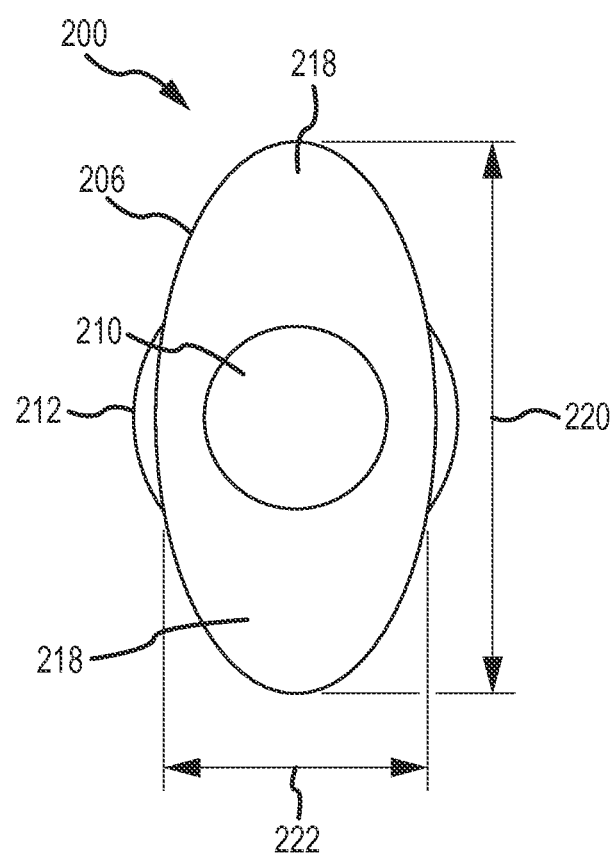
FIG. 4 is an end view of the same embodiment of an implant device as show in FIG. 2.
Figure 5:
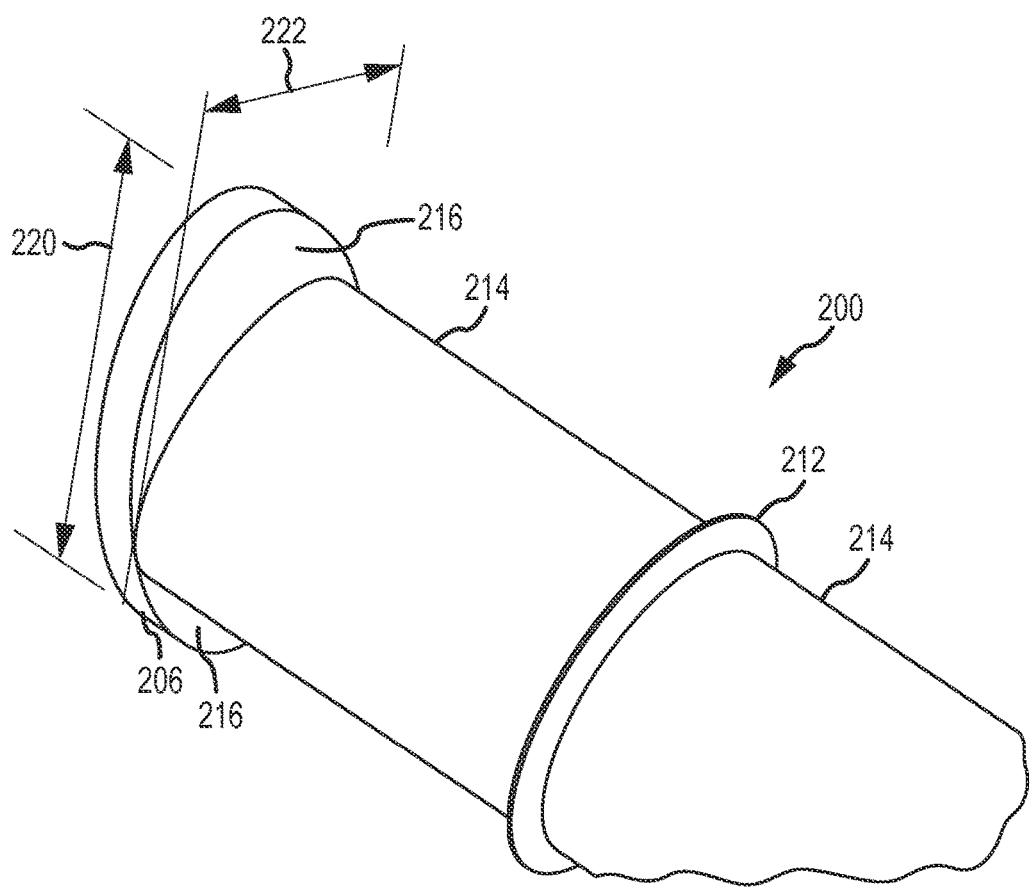
FIG. 5 is a partial perspective view of the same embodiment of an implant device as shown in FIG. 2.

The terms "lacrimal apparatus" and "lacrimal system" are used interchangeably herein to refer to the collection of physiological components that accomplish the production and secretion of lacrimal fluid to lubricate the eyeball, containment of lacrimal fluid in a reservoir of lacrimal fluid in the orbit and drainage of lacrimal fluid from the orbit to the nasal cavity. The lacrimal apparatus includes the lacrimal glands, the tear drainage system and the reservoir of lacrimal fluid located between the lacrimal glands and the tear drainage system. The reservoir of lacrimal fluid includes the eyelid margins and the conjunctival sac (and including the pool of tears in the lower conjunctival cul-de-sac that is sometimes referred to as the lacrimal lake). The tear drainage system includes the puncta, canaliculi and nasolacrimal duct (including the so-called lacrimal sac located at the top of the nasolacrimal duct) through which excess tears drain to Hasner's valve and into the nasal cavity. FIG. 1 shows generally the lacrimal apparatus. Lacrimal fluid is produced and secreted from lacrimal glands 102 to lubricate the surface of the eyeball 104 disposed within the orbit. Lacrimal fluid forms a coating over the eyeball 104 and is generally contained within the conjunctival sac (the space between the lower eyelid 106, upper eyelid 108 and eyeball 104 that is lined by the conjunctiva). Excess lacrimal fluid is conducted to the vicinity of the medial canthus (medial corner of the eye) and drains through the lacrimal puncta 110 into the lacrimal canaliculi 112 and into the lacrimal sac 114 of the nasolacrimal duct 116. The lacrimal fluid then drains from the nasolacrimal duct 116 through Hasner's valve and into the nasal cavity.

As used herein, a fistula between the lacrimal apparatus and a paranasal sinus refers to an artificially-created passage that fluidly connects the lacrimal apparatus with a paranasal sinus. Such a fistula may be surgically created. The paranasal sinuses include the frontal sinuses, maxillary sinuses, ethmoid sinuses and sphenoid sinuses, which are cavities contained within frontal, maxilla, ethmoid and sphenoid bones, respectively. The paranasal sinuses drain into the nasal cavity. FIG. 1 also shows the general proximity of the frontal sinus 122, maxillary sinus 124 and ethmoid sinus 126 relative to features of the lacrimal apparatus and some example fistula routes shown by dashed lines. A first example fistula route 130 is from the orbit to the frontal sinus. A second example fistula route 132 is from the orbit to the ethmoid sinus 126. A third example fistula route 134 is from the orbit to the maxillary sinus 124. A fourth example fistula route 136 is from the lacrimal sac 114 at the top of the nasolacrimal duct 116 to the ethmoid sinus 126. A fifth example fistula route 138 is from the nasolacrimal duct 116 at a location below the lacrimal sac 114 to the ethmoid sinus 126. A sixth example fistula route 140 is from the nasolacrimal duct 116 at a location below the lacrimal sac 114 to the maxillary sinus 124. The example fistula routes shown in FIG. 1 are for purposes of general illustration only and not to show precise locations where a fistula might be formed to connect a part of the lacrimal apparatus with the corresponding paranasal sinus. Although not shown in FIG. 1, example fistula routes to the sphenoid sinus include from the orbit to the sphenoid sinus and from the nasolacrimal duct 116 to the sphenoid sinus.

FIGS. 2-5 show one embodiment of an implant device, for example that may be implanted through a fistula at the first, second or third routes 130, 132, or 134 shown in FIG. 1. As shown in FIGS. 2-5, an implant device 200 has a proximal end 202 and a distal end 204 located on opposite longitudinal ends of the implant device 200. The implant device 200 includes a head 206 at the proximal end 202 and a conduit 208 extending from the head 206 to the distal end 204. An internal passage 210 extends from the proximal end 202 to the distal end 204, passing through the head 206 and the conduit 208. The internal passage 210 opens at the proximal end 202 and the distal end 204, thereby providing a passage through the entire longitudinal length of the implant device 200. The internal passage 210 of the embodiment shown in FIG. 2 has a cylindrical shape with a uniform circular cross-section (transverse to the length of the implant device 200), and the width of the internal passage is equal to the diameter of the circle of the cross-section and is uniform along the length of the implant device 200. The length of the implant device 200 is the minimum distance longitudinally along the implant device 200 between the proximal end 202 and the distal end 204, and will typically be equal to the distance along an axis of the internal passage 210 from the proximal end 202 to the distal end 204. The implant device 200 includes multiple anchor protrusions 212 on an exterior of the conduit 208. In the embodiment shown in FIGS. 2-5, the anchor protrusions 212 are in the form of spaced circumferential ridges that each extends around the entire circumference of the conduit 208. Adjacent the circumferential ridges of the anchor protrusions 212 are areas of recess 214 on the exterior of the conduit 208.

The head 206 has a flanged tissue engagement surface 216 on a side of the head 206 disposed toward the conduit 208, and which flanged tissue engagement surface 216 is advantageously configured to engage tissue adjacent the proximal end of fistula and to prevent the proximal end 202 of the implant device 200 from migrating into the fistula following implantation. On the side of the head 206 opposite the flanged tissue engagement surface 216 is a face surface 218 of the head 206, which face surface 218 is disposed away from tissue engaged by the flanged tissue engagement surface 216 when the implant device is implanted. The head 206 has a first dimension 220 and a second dimension 222 on both the flanged tissue engagement surface 216 and the face surface 218. The first dimension 220 is the length of the respective surface and the second dimension is the width of the respective surface. Such length and width dimensions may also be referred to as major and minor dimensions. The first dimension 220 of a surface 216 or 218 corresponds to the maximum separation distance between points on the outer edge of the surface (maximum cross dimension across the head), and the second dimension 222 of the surface 216 or 218 corresponds to the maximum separation distance between points on the outer edge of the surface that are on a line transverse (perpendicular) to the first dimension. Conveniently, the face surface 218 and the flanged tissue engagement surface 216 may be made with corresponding outer edges, so that the opposing surfaces 216 and 218 have substantially equal length and width dimensions, although such is not required. The first dimension 220 and the second dimension 222 may be referred to generally as the length and width, respectively, of the head 206 when the surfaces 216 and 218 have corresponding shapes, as is the case for the embodiment shown in FIGS. 2-5. When the surfaces 216 and 218 do not have corresponding shapes, the length and width dimensions of the head will be different from one or more of the length and width dimensions of the surfaces 216 and 218. The head 206 has a depth dimension 223 between surfaces 216 and 218.

With continued reference to FIGS. 2-5, the conduit 208 has a first exterior width 224 that is a maximum exterior width of the conduit 208 as defined by the maximum extents of the anchor protrusions 212 transverse to the length of the conduit 208. The conduit 208 has a second exterior width 226 that is a minimum exterior width of the conduit 208 defined between the most recessed portions of the areas of recess 214. In the embodiment shown in FIGS. 2-5, the height of the anchor protrusions 212 is equal to one-half the difference between the first exterior width 224 and the second exterior width 226 of the conduit 208. In the configuration of the head 206 shown in FIGS. 2-5, the first dimension 220 of the head is larger than both the first exterior width 224 and the second exterior width 226 of the conduit 208, while the second dimension 222 of the head is approximately equal to the second exterior width 224 of the conduit 208.

With continued reference to FIGS. 2-5, the anchor protrusions 212 are in the form of spaced circumferential ridges having a width that is at a maximum at the bottom of the ridges located adjacent the areas of recess 214, and which width tapers to a minimum at the top of the ridges 212 located away from the recess areas 214. Other configurations for anchor protrusions are possible, and all anchor protrusions on an implant device need not be of the same size, geometry or height. Likewise, areas of recess may have varying configurations, and not all recesses on an implant device need to be the same size or configuration. The implant device 200 has a length 228 including the depth 223 of the head 206 and the length of the conduit 208. The anchor protrusions 212 are on a longitudinal portion 230 of the conduit 208.

Figure 6:
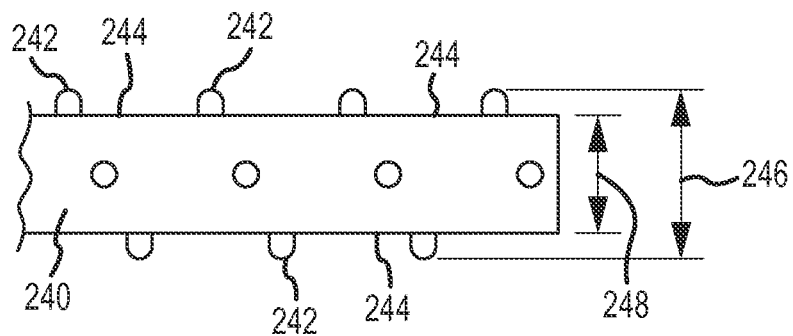
FIG. 6 is a partial side view of an embodiment of an implant device.
Figure 7:
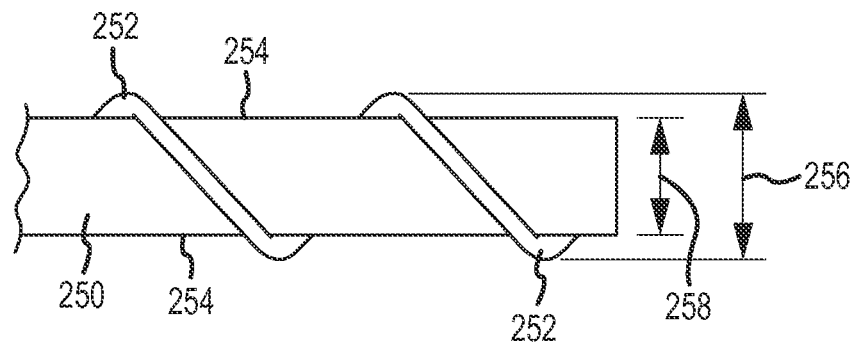
FIG. 7 is a partial side view of an embodiment of an implant device.

Referring now to FIG. 6, an alternative embodiment is shown of a conduit 240 of an implant device having anchor protrusions 242 in the form of knobs, or buttons, and areas of recess 244 adjacent the anchor protrusions 242. The conduit 240 has a first exterior width 246 defined by the anchor protrusions 242 and a smaller, second exterior width 248 defined by the areas of recess 244. An example of another configuration for anchor protrusions is shown in FIG. 7. As shown in FIG. 7, a conduit 250 of an implant device has anchor protrusions 252 and areas of recess 254 on the exterior surface of the conduit 250. The anchor protrusions 252 are in the form of a continuous spiral ridge extending along a portion of the longitudinal length of the conduit 250. The conduit 250 has a first exterior width 256 defined by the anchor protrusions 254 and a smaller, second exterior width 258 defined by the areas of recess 254. As with the embodiments shown in FIGS. 2-5, the conduit embodiments shown in FIGS. 6 and 7 include a height of the anchor protrusions that is equal to one half the difference between the larger and smaller outer diameters of the respective conduits. As will be appreciated from the embodiments of FIGS. 6 and 7, the first exterior width is determined as the width of an envelope volume that contains the anchor protrusions.

Figure 8:
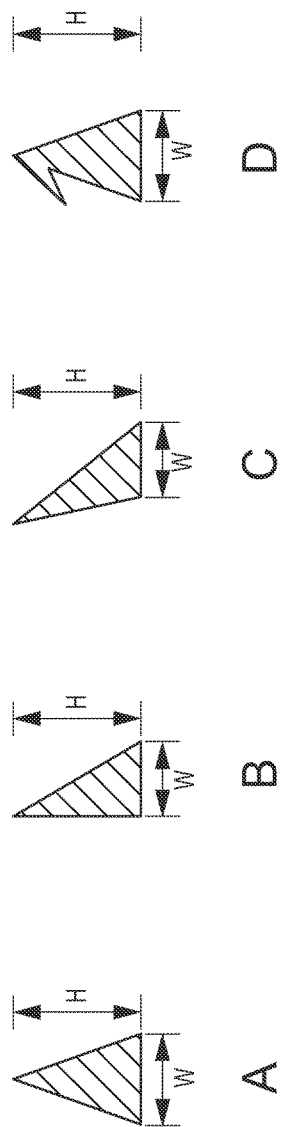
FIG. 8 is an illustration of cross-sections of various configurations for anchor protrusions for an implant device.

FIG. 8 shows examples of some shapes for anchor protrusions that include a tapering width in a direction from the base of the anchor protrusion toward a top of the anchor protrusion. FIG. 8 shows cross-sections of anchor protrusion configurations (designated A-D), each having a greater width at the base than at the top. The height (H) and base width (W) of the anchor protrusions are indicated in FIG. 8.

FIG. 9 shows some different example configurations (designated E-H) for a head for an implant device. For each head configuration, the length dimension (L) and width dimension (W) of the head configurations are shown. The heads of configurations E-H are shown on end showing the face surface (surface facing away from the fistula when implanted) and the opening of the internal passage at the proximal end of the implant device. Configurations F-H, with a larger length than width, are advantageously configured for use with fistulas opening into the orbit between the medial canthus and the medial side of the adjacent eyeball, for example between the plica semilunaris and the lacrimal caruncle, and preferably with the length dimension of the head extending generally in a direction from the bottom of the orbit toward the top of the orbit next to the eyeball, and for configuration H with the concave side of the crescent disposed toward the eyeball and the convex side of the crescent disposed towards the lacrimal caruncle.

Figure 10:
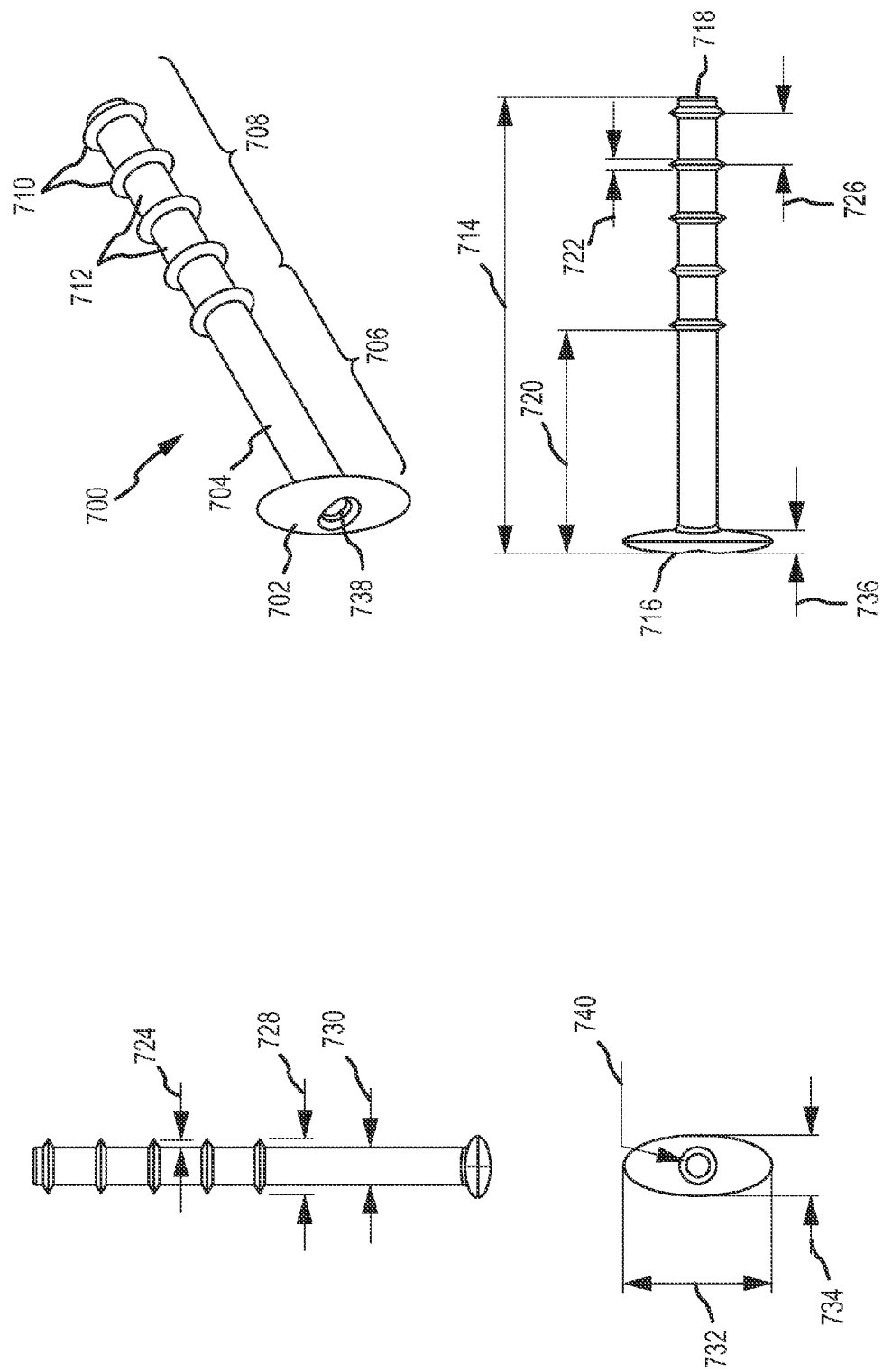
FIG. 10 shows perspective, top, side and end views of an embodiment of an implant device.
Figure 11:
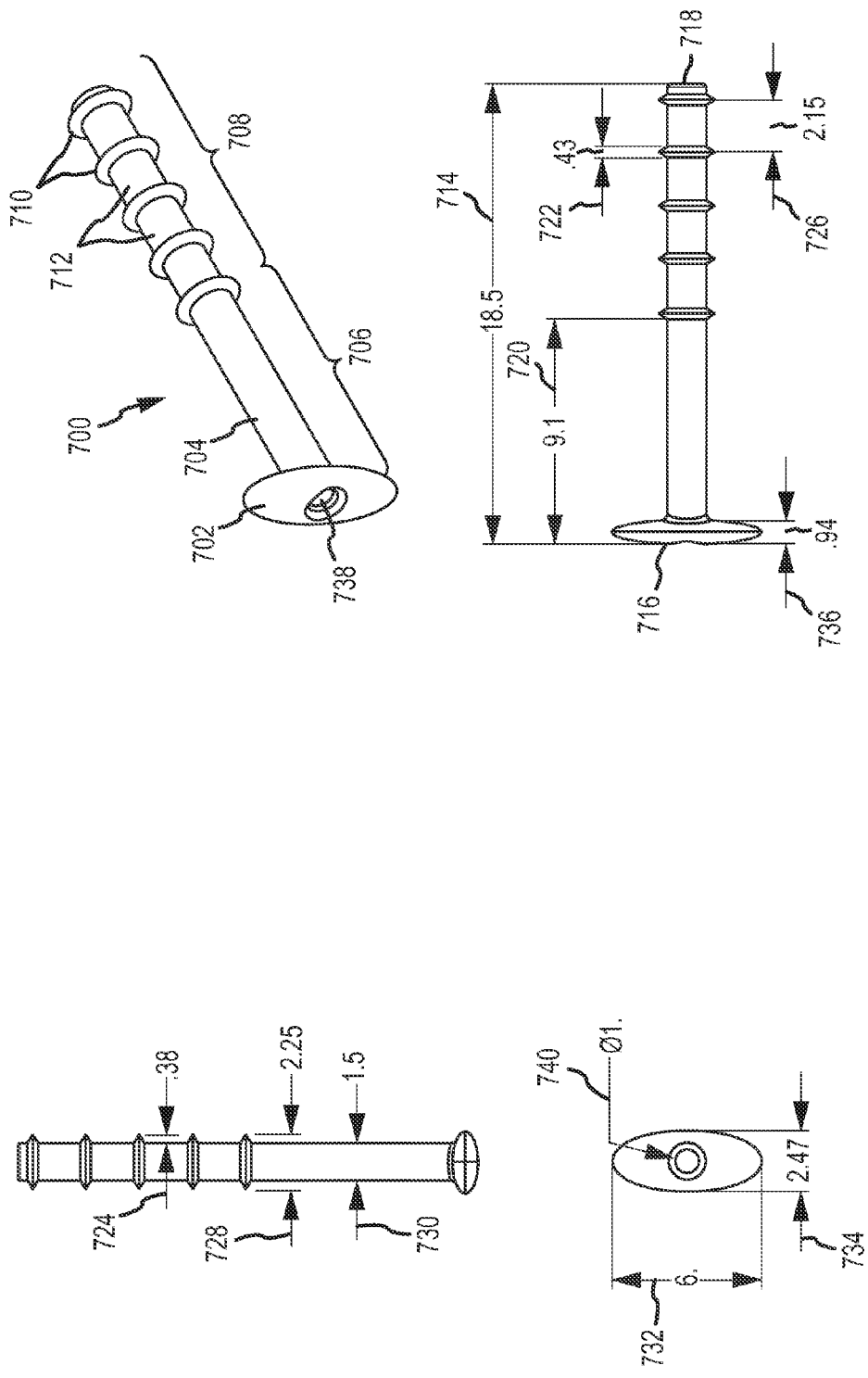
FIG. 11 shows perspective, top, side and end view of an embodiment of an implant device showing some possible example dimensions.

FIG. 10 shows an implant device 700 with a head 702 and a conduit 704. The conduit 704 includes a first longitudinal portion 706 and a second longitudinal portion 708 disposed distal of the first longitudinal portion 706. The first longitudinal portion 706 includes a smooth exterior surface and the second longitudinal portion 708 includes an anchoring surface feature including anchor protrusions 710, in the form of spaced circumferential ridges, and recess areas 712 between the anchor protrusions 710. The length of the first longitudinal portion 706 located before the beginning of the anchoring surface feature of the second longitudinal portion 708 may advantageously be disposed in conjunctival tissue adjacent the head 702 when implanted to "float" for patient comfort. The anchoring features of the second longitudinal portion 708 may advantageously be located a distance from the head 702 so that one or more of the anchor protrusions 710 are located in the vicinity of the paranasal sinus bone wall that is penetrated by the implant device 700 when implanted, preferably with one or more of the anchor protrusions disposed on each side of the bone. In the embodiment shown in FIG. 10, the exterior width of the conduit 704 is substantially the same for the whole length of the first longitudinal portion 706 and in the recess areas 712 of the second longitudinal portion 708. The conduit 704 has a circular cross-section, so that the exterior width of the conduit 704 at any location along the conduit 704 is represented by the diameter of the circular cross-section of the conduit 704 at that location. As shown in FIG. 10, the implant device 700 has a length 714 from a proximal end 716 to a distal end 718 of the implant device 700. The beginning of the second longitudinal portion 708 is located a distance 720 distal from the proximal end 716. The anchor protrusions 710 have a width 722 at the base of the anchor protrusions 722 and a height 724 above the adjacent recess areas 712. The anchor protrusions 710 are spaced on a center-to-center spacing 726. The conduit 704 has a maximum exterior width 728 corresponding with the tops of the anchor protrusions 710, equal to the diameter of the circle of the cross-section through the conduit 704 at the top of the anchor protrusions 710. The conduit 704 has a minimum exterior width 730 along the length of the first longitudinal portion 706 and in the recess areas 712 of the second longitudinal portion 708 of the conduit 704, and which is equal to the diameter of the circular cross-section at those locations. The head 702 has a length dimension 732, a width dimension 734 and a depth dimension 736. The implant device 700 has an internal passage 738 extending between the proximal end 716 and the distal end 718 and through the length of the conduit 704. The internal passage 738 has a width 740, which in this embodiment is equal to a diameter of the circular cross-section of the internal passage 738. FIG. 11 shows the same implant device 700 as shown in FIG. 10 with some exemplary dimensions, in millimeters, for one nonlimiting example for a configuration for the implant device 702.

Figure 12:
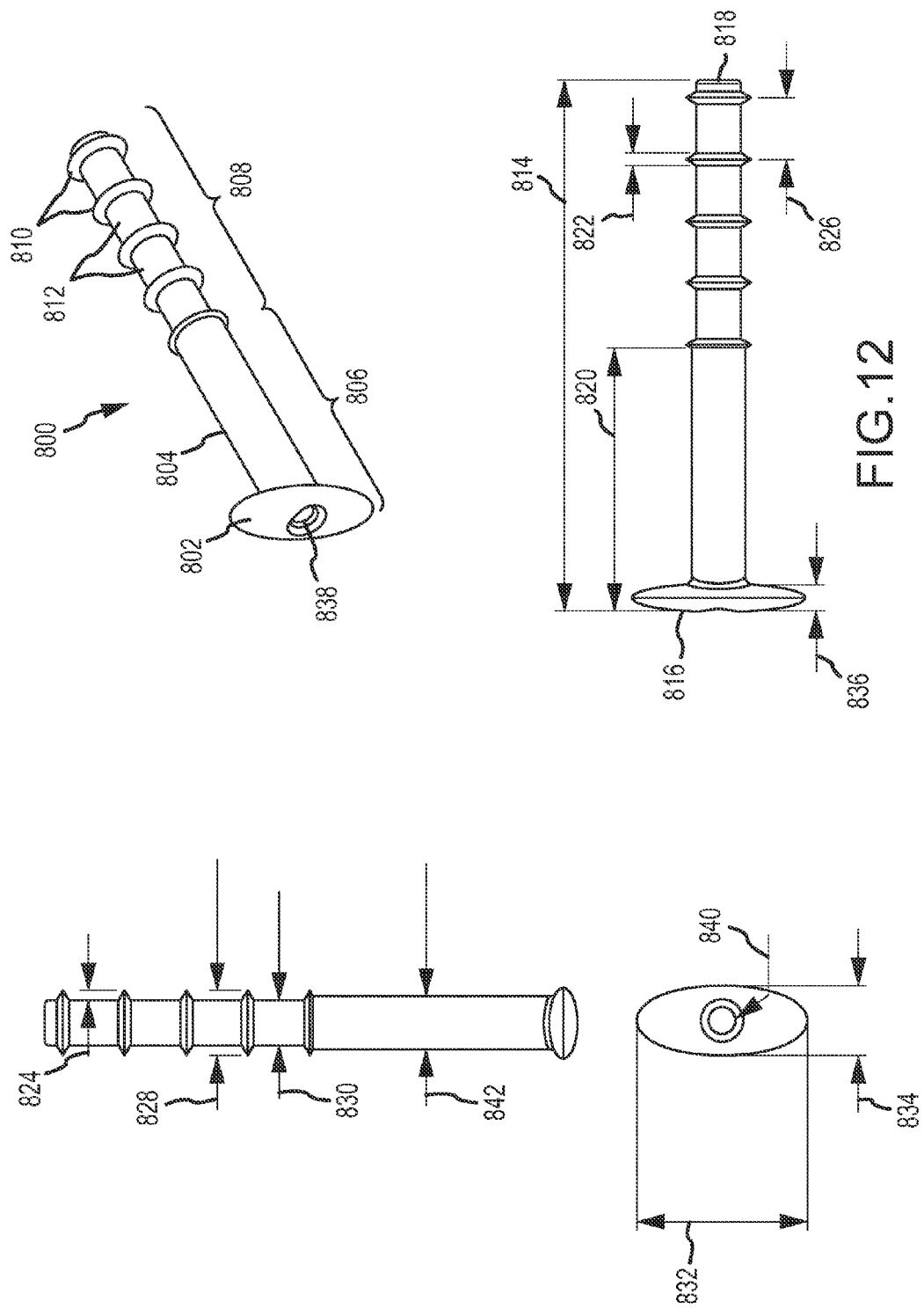
FIG. 12 shows perspective, top, side and end views of an embodiment of an implant device.

FIG. 12 shows an implant device 800 that is similar to the implant device 700 shown in FIGS. 10 and 11, except including a first longitudinal portion of a conduit having a thicker wall than recess areas of the anchoring surface feature of a second longitudinal portion of the conduit. The thicker wall in the first longitudinal portion of the conduit provides added rigidity to that portion of the conduit to facilitate pushing the implant device 800 into place during an implantation procedure, while the thinner wall in the recess areas of the second longitudinal portion of the conduit permit that portion to more easily deform and fit through a fistula during implantation and then to expand to engage tissue and anchor the implant device 800. More specifically as shown in FIG. 12, the implant device 800 includes a head 802 and a conduit 804. The conduit 804 has a first longitudinal portion 806 and a second longitudinal portion 808 located distal of the first longitudinal portion 806. The first longitudinal portion 806 includes a substantially smooth exterior surface with a substantially constant exterior width, which is the diameter of the circular cross-section of the conduit 804 along the first longitudinal portion 806. The second longitudinal portion 808 includes an anchoring surface feature including anchor protrusions 810, in the form of circumferential ridges, and recess areas 812 in the spaces between the anchor protrusions 810. Various dimensions of the implant device 802 are illustrated in FIG. 12, similar to the illustration provided for the implant device 700 in FIG. 10. The implant device 800 has a length 814 from a proximal end 816 to a distal end 818 of the implant device 800. The beginning of the second longitudinal portion 808 is located a distance 820 distal of the proximal end 816. The anchor protrusions have a width 822 at the base and a height 824 above the adjacent recess areas 812. The anchor protrusions are spaced on a center-to-center spacing 826. The conduit 804, and also the second longitudinal portion 808, has a maximum exterior width 828 occurring at the tops of the anchor protrusions 810, and equal to the diameter of the circular cross-section of the conduit 804 through the tops of the anchor protrusions 810. The conduit 804, and the second longitudinal portion 808, of the conduit 804 have a minimum exterior width 830 located at the recess areas 812. The head 802 has a length dimension 832, a width dimension 834 and a depth dimension 836. The implant device 800 has an internal passage 838 extending between the proximal end 816 and the distal end 818 and through the length of the conduit 804. The internal passage 838 has a width 840, which in the embodiment shown in FIG. 12 is equal to a diameter of the circular cross-section of the internal passage 838.

Figure 13:
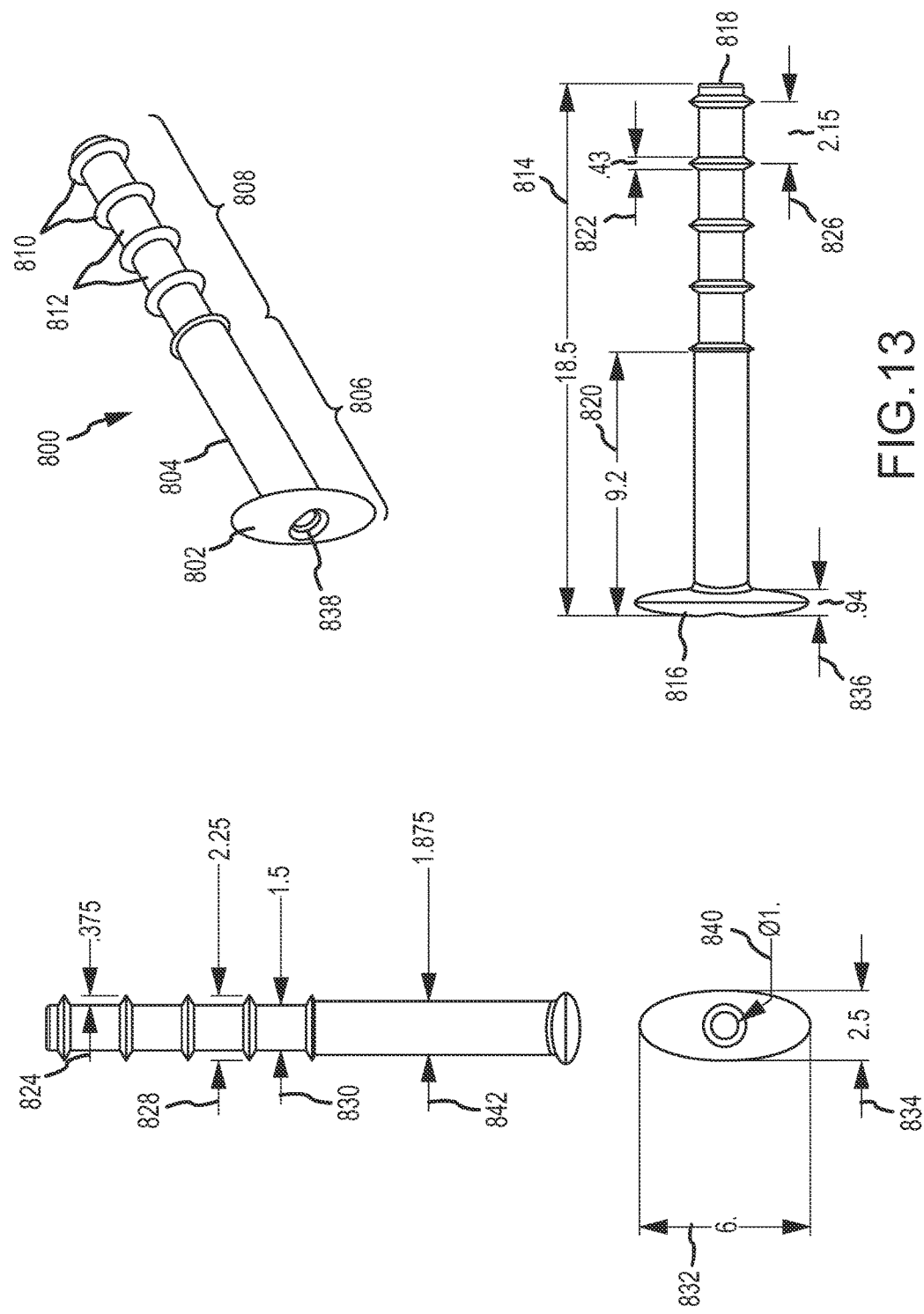
FIG. 13 shows perspective, top, side and end view of an embodiment of an implant device showing some possible example dimensions.

With continued reference to FIG. 12, the wall thickness of the conduit 804, (thickness of the wall between the internal passage 838 and the exterior surface of the conduit 804) is greater along the first longitudinal portion 806 than in the recess areas 812 of the second longitudinal portion 808. The internal passage 838 has a constant width along the length of the conduit 804, such that the greater wall thickness of the conduit 804 along the first longitudinal portion 806 results in an exterior width 842 that is larger than the minimum exterior width 830 in the recess areas 812. The maximum exterior width 828 at the anchor protrusions 810 is larger than the exterior width 842 along the first longitudinal portion 806. FIG. 13 shows some exemplary dimensions, in millimeters, for one nonlimiting example for a configuration of the implant device 800.

Figure 20:
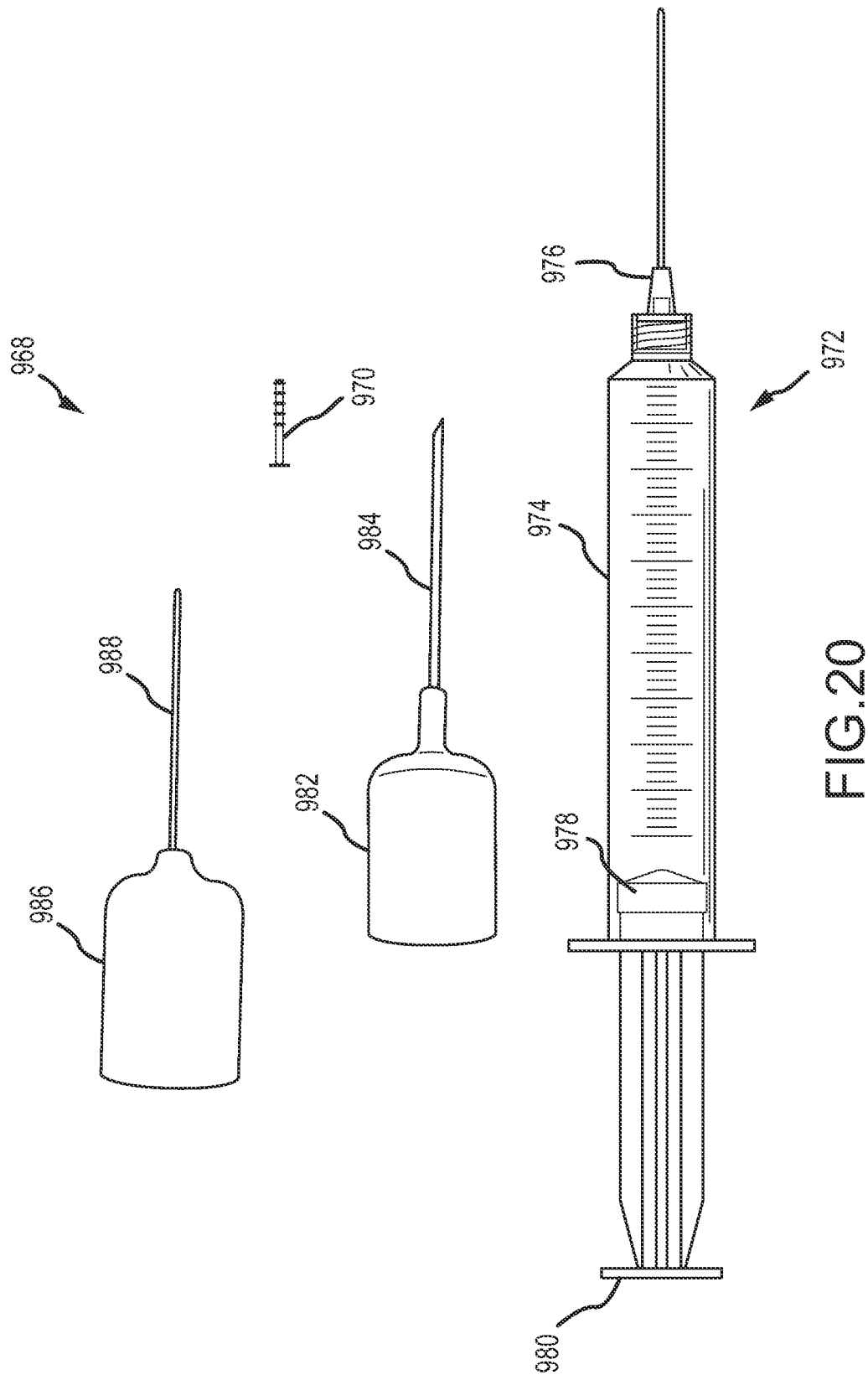
FIG. 20 illustrates an embodiment of a kit useful for implanting a paranasal sinus access implant device and providing medical treatments using such a paranasal sinus access implant device.
Figure 21:
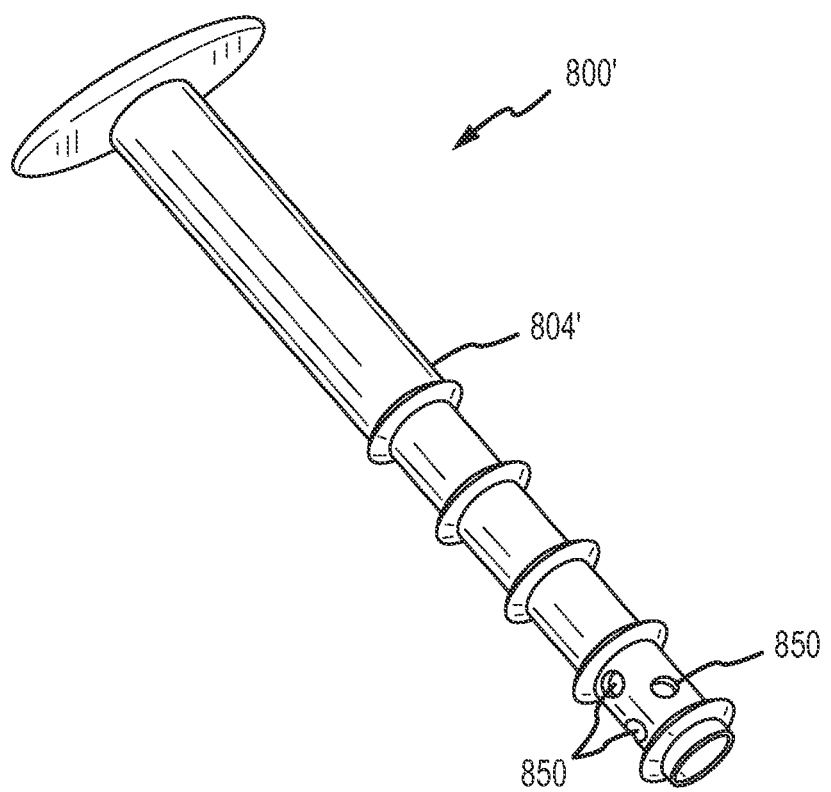
FIG. 21 is a perspective view of an embodiment of an implant device.

FIG. 21 shows a variation on the implant device 800 of FIG. 20. The implant device 800' of FIG. 21 has the same features as the implant device 800 of FIG. 20, except that the implant device 800' includes a plurality of side openings 850 (which may also be referred to as holes, apertures or ports) through the wall of a distal portion of the conduit 804'. The side openings 850 may be located on a portion of the conduit wall that would be disposed in the paranasal sinus when the implant device 800' is implanted, such that the side openings 850 may provide a passage for fluid communication between the internal passage of the implant device 800' and the paranasal sinus even if the distal opening of the internal passage at the distal end of the conduit 804' were to become blocked or restricted for some reason. In the particular implementation shown in FIG. 21, the implant device 800' the side openings 850 are located in a recess area between a pair of circumferential ridges of an anchoring surface feature of the conduit 804'. FIG. 21 shows the side openings 850 located in only one recess area between one pair of circumferential ridges, but one or more similar side openings could also or alternatively be located in a more proximal recess area between a different pair of the circumferential ridges.

Figure 14:
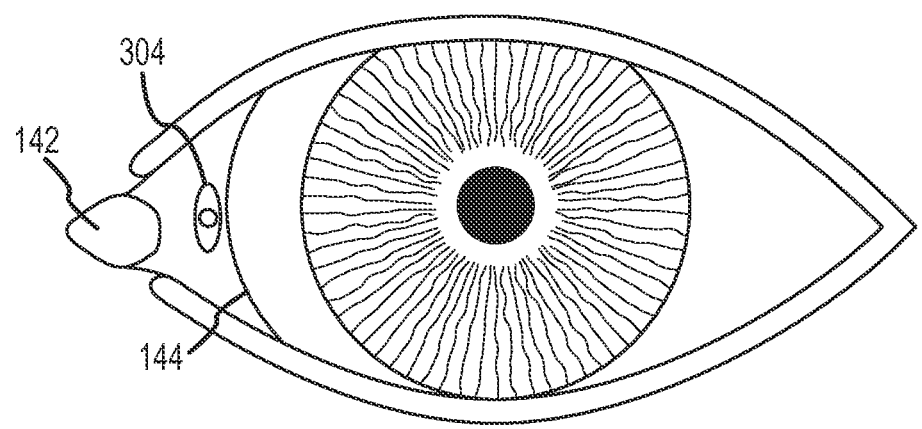
FIG. 14 is an illustration showing an embodiment for placement of an implant device with a head of the implant device located within the orbit between the lacrimal caruncle and plica semilunaris.

FIG. 14 shows an example of an implant device with a conduit passing through a fistula formed from the orbit subconjunctivally between the lacrimal caruncle 142 and the plica semilunaris 144, and showing an example location for the head 304 of the implant device disposed in the orbit between the lacrimal caruncle 142 and the plica semilunaris 144. The head 304 is shown with an elongated configuration, such as for example a head configuration shown in any of FIGS. 2-5, FIGS. 10-13, or configurations F-H shown in FIG. 11.

Referring now to FIGS. 15-18, some examples of surgical procedures involving forming a fistula and implanting an implant device to provide access to a paranasal sinus, and some example surgical tools for use therewith, will now be described.

Figure 15:
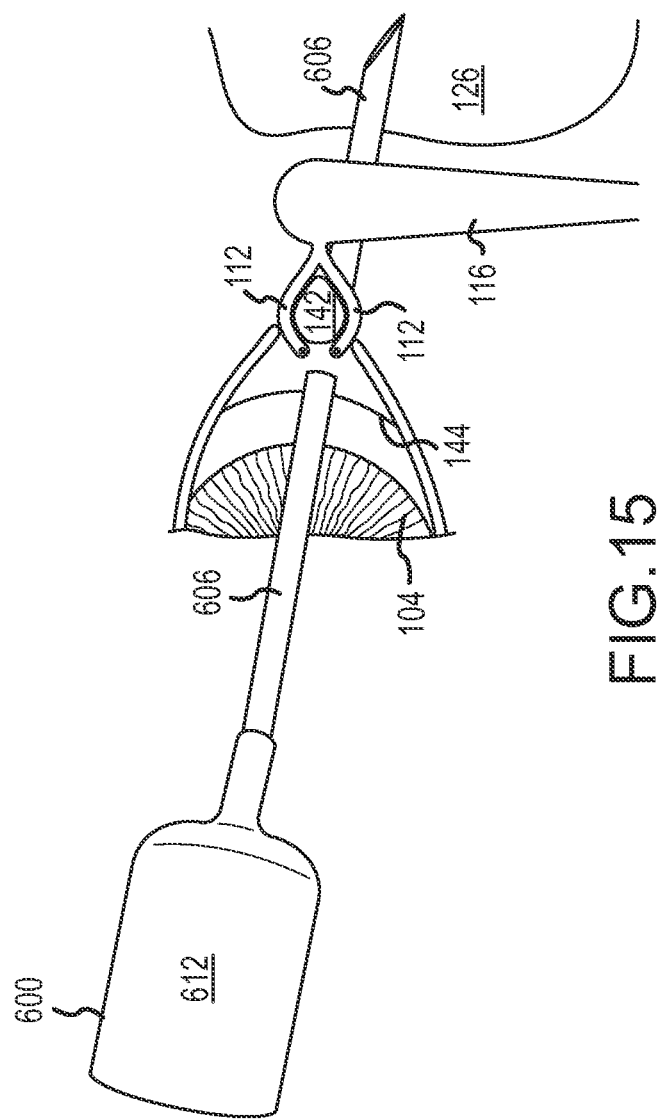
FIG. 15 is an illustration showing use of a surgical tool, in the form of a cutting tool, to form a fistula between the orbit and an ethmoid sinus during a surgical procedure.

In FIG. 15 a surgical tool, in the form of an entry tool 600 is shown in the process of making a fistula through tissue between the lacrimal caruncle 142 and the plica semilunaris 144. Numbering of anatomical parts is the same as in FIG. 1. The fistula is formed through tissue between the conjunctival sac in the orbit and the ethmoid sinus 126. The route for the fistula would be consistent with general fistula route 132 as shown in FIG. 1. The entry tool 600 includes a hollow working member 606 with a hollow cutting distal tip 610 with a shape suitable to cut away tissue to form a fistula from the conjunctival sac to the ethmoid sinus 126. The entry tool 600 may also be referred to as a cutting tool and the working member may also be referred to as a cutting member. The entry tool 600 includes a hand-manipulable handle 612. The handle 612 may be advanced or retracted to advance or retract the hollow working member 606. As shown in FIG. 15, the distal cutting tip 610 has been advanced from a location in the conjunctival sac between the caruncle 142 and the plica semilunaris 144 to form a fistula between the conjunctival sac and the ethmoid sinus 126. As shown, the fistula passes behind the caruncle 142, canaliculi 112 and nasolacrimal duct 116 to access the ethmoid sinus 126.

Figure 16:
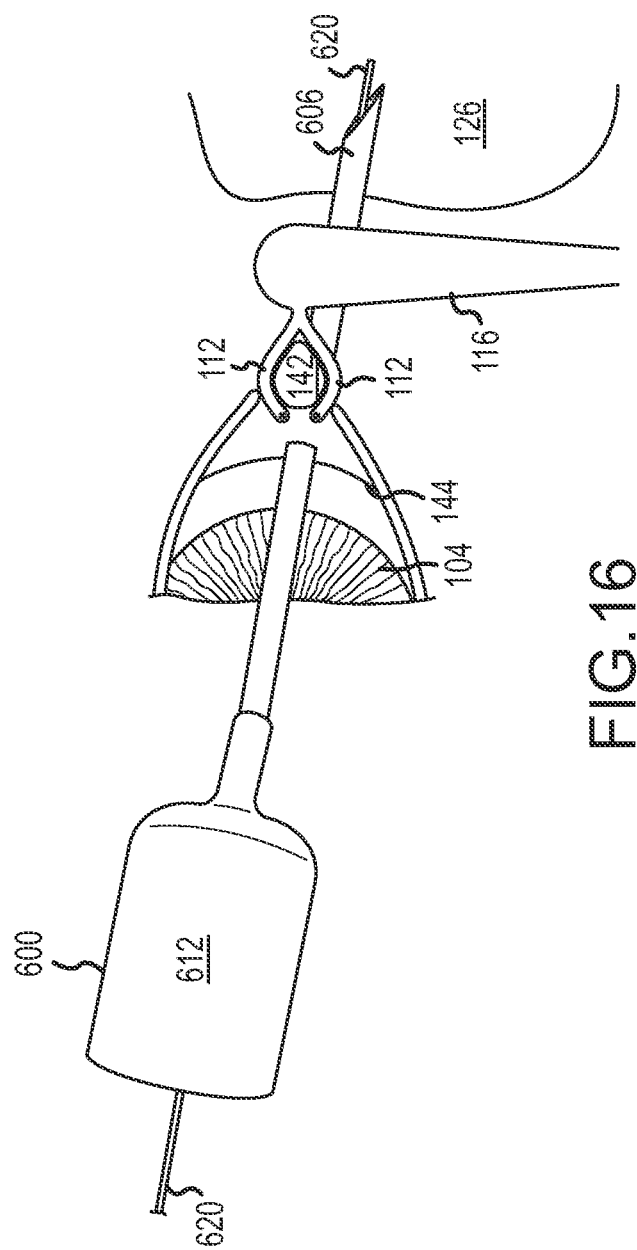
FIG. 16 is an illustration showing insertion of a guide wire following formation of a fistula during a surgical procedure.
Figure 17:
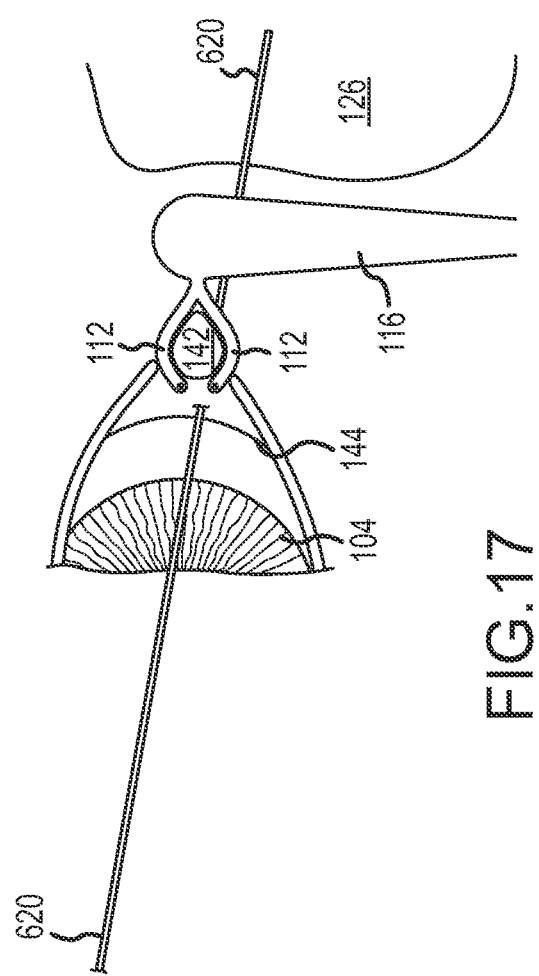
FIG. 17 is an illustration showing a guide wire in place as a guide to a fistula during a surgical procedure.

After the entry tool 600 has been used to initially form a fistula to the ethmoid sinus 126, then a guide wire or other guide member may be inserted through an internal passage extending through the handle 612 and the hollow working member 606. FIG. 16 shows a guide wire 620 inserted through the handle 612 and the working member 606. After insertion of the guide wire 620, entry tool 600 may be retracted and removed from the fistula, leaving the guide wire 620 in place as a guide to and through the fistula, as shown in FIG. 17. The guide wire 620 is now available for guiding additional tools to and through the fistula into the ethmoid sinus 126.

Figure 18:
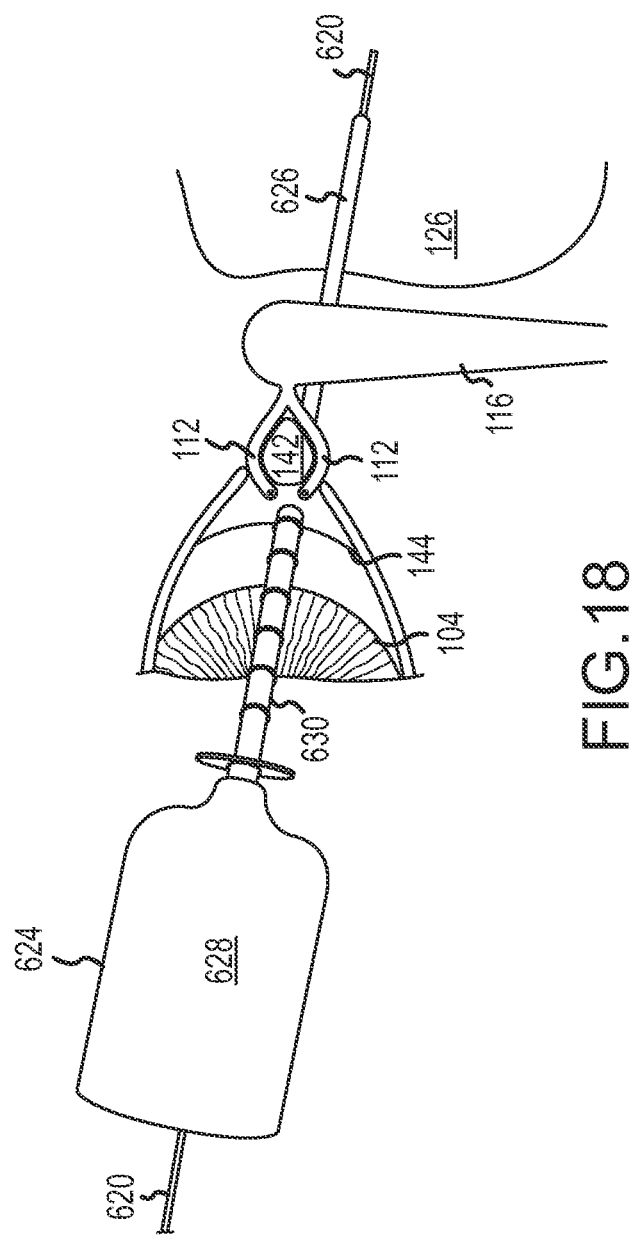
FIG. 18 is an illustration showing use of a surgical tool, in the form of a carrier tool, for implantation of an implant device during a surgical procedure.
Figure 19:
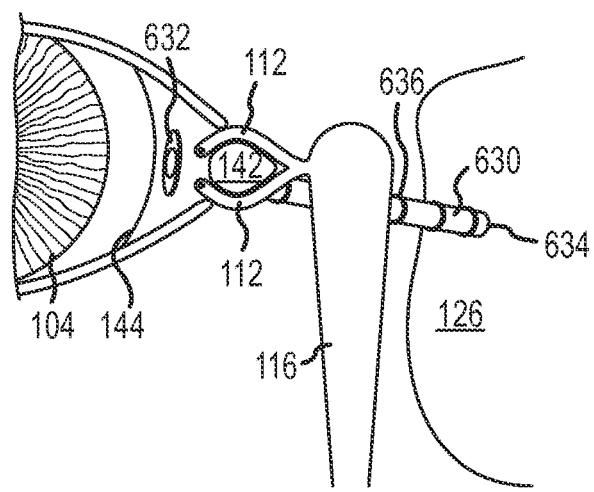
FIG. 19 is an illustration showing placement of an implant device following implantation during a surgical procedure.

With reference now to FIG. 18, the guide wire 620 has been used to guide a surgical tool, in the form of an implant tool 624. The implant tool may also be referred to as a carrier tool. The implant tool 624 includes a hollow working member 626 and a hand-manipulable handle 628. The working member 626 may have a blunt distal tip, as shown in FIG. 18, since the working member 626 may not need to cut additional tissue following formation of the fistula using the entry tool 600, provided that the fistula has already been formed to a final desired size. The working member 626 may also be referred to as a carrier member. The implant tool 624 includes an internal passage passing through the handle 628 and the hollow working member 626. As shown in FIG. 18, the guide wire 620 has been threaded through the internal passage of the implant tool 624 to guide the hollow working member 626 to and through the fistula and into the ethmoid sinus 126. An implant device 630 is mounted on the hollow working member 626 of the implant tool 624. FIG. 18 shows the implant tool 624 advanced to a point where the distal end of the implant device 630 is in the vicinity of the proximal end of the fistula opening into the conjunctival sac. From this position, the implant device 630 may be advanced into the fistula with a head of the implant device 630 disposed adjacent the conjunctiva in the conjunctival sac and a distal end of the implant device 630 extending into the ethmoid sinus 626. For example, a surgeon may slide the implant device 630 down the hollow working member 626 for placement through the fistula for implantation or the surgeon may advance the handle 628 to have the handle push the implant device 630 into the fistula for implant placement. The outside diameter of the hollow working member 626 may be sized to closely fit within the inside diameter of the implant device 630 to help prevent the implant device 630 from bunching-up and laterally deforming as the implant device is pushed into the fistula. The handle 628 and the hollow working member 626 form a carrier for the implant device 630. The handle 628 may be retracted and the hollow working member 626 disengaged from the implant device 630 after the implant device 630 has been appropriately positioned for implantation through the fistula. FIG. 19 shows the implant device 630 as implanted and following disengagement of the hollow working member 626 of the implant tool 624. As implanted, a head 632 at the proximal end of the implant device 630 is located adjacent the conjunctiva in the conjunctival sac within the orbit between the caruncle 142 and the plica semilunaris 144 and the distal end 634 of the implant device 630 is located in the ethmoid sinus 126. Some anchor protrusions 636 of the conduit of the implant device 630 are disposed within the fistula to engage tissue and help anchor the implant device 630. The implant device 630 may be used to provide access to the ethmoid sinus 126 to perform medical procedures or treatments, for example to administer a treatment composition to the ethmoid sinus or to aspirate fluid from the ethmoid sinus.

The procedure as described with reference to FIGS. 15-19 permits the working member 606 of the entry tool 600 to have a larger diameter working member 626 to form a fistula of appropriate size for accommodating the implant device 630 which is then implanted in a separate step using the implant tool 624 with the implant device 630 carried on to the working member 626, which may advantageously have a smaller diameter than the working member 606 used to form the fistula. As an alternative, an intermediate step to dilate the fistula or to cut away additional tissue to a desired hole size for implantation may be performed between initially forming a fistula with the entry tool 600 and implanting the implant device 630 using the implant tool 624.

Referring again to FIG. 15, optionally, one or more procedures may be performed prior to retracting the hollow working member 606. One or more fluids may be injected through the hollow working member 606. For example, contrast media may be injected through the hollowing working member 612 and may be imaged to confirm that the fistula has been formed to the proper location prior to proceeding with implantation.

The cutting may be performed, for example, with a cutting tool such as a needle or cannula that cuts tissue or a drill that drills out the tissue. A method may include cutting an initial hole at the location of the desired fistula, and then using a guide member and further tools to complete an implantation procedure. For example, the initial cut may be to make a preliminary hole and a larger gauge needle or cutting cannula may be guided by the guide member to cut the fistula to the final desired size for implantation of the implant device. Alternatively, the initial hole that is cut may be of a final desired size for implantation of the implant device. After the hole has been made to the desired size, the guide member may then be used to guide the implant device or a carrier tool on which the implant device is mounted to the fistula for implantation of the implant device. As one example, a small gauge needle may be used to form an initial cut, and a guide wire may then be inserted through the needle and into the fistula to maintain control of the fistula. The smaller gauge needle may then be retracted and the second cutting tool, in the form of a larger gauge needle, may be slid over the guide wire and conducted to the proper location to cut the fistula to the proper size for implantation of the implant device. A kit for performing such an operation my include the implant device, the smaller gauge needle, the guide wire (as the guide member) and the larger gauge needle as the cutting tool for making the fistula to the final desired size. As another example, the initial cutting tool, or a portion thereof may be used as the guide member for the subsequent cutting tool. For example, the initial cut may be made using a smaller gauge needle having a handle, such as a spinal needle or similar design. Following the initial cut, the handle, or head, may be cut off and removed from the smaller gauge needle and a cutting tool in the form of a larger gauge needle may then be slid over the smaller gauge needle to cut the hole to the final desired size for the fistula. The larger gauge needle may then be retracted and the implant device may be slid over the smaller gauge needle and conducted to the proper location for implantation. A kit for performing such an operation may include the implant device, the smaller gauge needle (which serves as the guide member) and the larger gauge needle as the cutting tool for making the fistula to the final desired size. Alternatively, a kit may include a single cutting tool (e.g., hollow needle or cutting cannula) sized to cut a hole of the final desired size through which the implant device is to be implanted, and without enlargement by further cutting or dilation.

Referring now to FIG. 20, an example embodiment of a kit is shown that includes components for implanting a paranasal access implant device and delivering a treatment composition to a paranasal sinus through the implant device. As shown in FIG. 20, a kit 968 includes a paranasal sinus access implant device 970. The implant device 970 may for example have any design according to or with features shown or described in relation to any of FIGS. 2-13, or may have a different design. The kit also includes a paranasal sinus fluid manipulation tool 972, which includes a fluid dispenser in the form of a syringe 974 and a fluid transmission attachment 976 including a fluid ejection member 977 in the form of a blunt tip hollow needle. The fluid transmission attachment 976 includes an engagement structure at a distal end to engage with a head on a proximal end of the implant device 970 to facilitate transmission of fluid from inside a barrel of the syringe 974 to be ejected from a distal tip of the fluid ejection member 977. The syringe 974 includes a piston 978 disposed in the barrel of the syringe 974 and that is hand manipulable by advancement or retraction of a plunger 980 to move the piston 978 in the syringe barrel to create pressure to expel fluid from the syringe barrel through the fluid transmission attachment 976 or to create a vacuum to suction fluid through the fluid transmission attachment 976 into the syringe barrel. The fluid manipulation tool 972 may be provided with the syringe 974 and the fluid transmission attachment 976 assembled as shown in FIG. 20, or may be provided with the syringe 974 and the fluid transmission attachment 976 as separate, disassembled pieces that are assemblable into the assembly as shown in FIG. 20. In some preferred implementations, the syringe 974 may be prefilled with a treatment composition disposed inside the barrel of the syringe 974. Such a prefilled syringe 974 may be provided in the kit 968 assembled with the fluid transmission attachment 976 as shown in FIG. 20, and preferably with a protective cap covering the fluid transmission attachment 976, and which cap is removable by a medical practitioner for use of the fluid manipulation tool 972 to administer a treatment composition to a patient in which the implant device 970 has been implanted to provide access to a paranasal sinus. A treatment composition disposed in the barrel of the syringe 974 may be an irrigation liquid or a drug composition, for example as previously described.

The kit 968 as shown in FIG. 20 also includes tools for forming a fistula between the lacrimal apparatus in the orbit and a paranasal sinus, for example a frontal, maxillary or ethmoid sinus. As shown in FIG. 20, the kit 968 includes a cutting tool 982 having a hollow cutting member 984 (e.g., hollow needle) for cutting away tissue to form a fistula of a size suitable for implantation of the implant device 972 without enlargement by further cutting or dilation. Alternatively a kit could include a cutting tool with a smaller gauge cutting member or piercing member to form an initial hole and one or more additional tools (e.g., cutting tool with larger gauge cutting member and/or dilator) may be included in a kit to enlarge the initial hole to a final desired size for implantation. The cutting tool 982 may for example have a design according to or including features as shown or described in relation to either of FIGS. 15 and 16, or may be of a different design.

The kit 968 as shown in FIG. 20 also includes a carrier tool 986 having an carrier member 988, which has an outside diameter sized for insertion of the carrier member 988 through the internal passage of the implant device 970 to mount the implant device 970 on the carrier member 988 to carry the implant device 970 for implantation after a fistula has been formed to a desired size. The carrier tool 986 may for example have a design according to or including any features as shown in or described in relation to FIG. 18 or may be of a different design. The carrier tool 986 and the implant device 970 may be provided in the kit 968 as separate, assemblable pieces such as is shown in FIG. 20. Alternatively, the carrier tool 986 and the implant device 970 may be provided in the kit with the implant device 970 pre-mounted on the carrier member 988 in a configuration ready for use in an implantation procedure.

The fluid ejection member 977 is configured to be inserted into an internal passage that extends through the implant device 970. After implantation of the implant device 970 to provide access to a paranasal sinus, the fluid ejection member 977 may be inserted into the internal passage from the proximal end of the implant device 970 that is disposed in the orbit following implantation. After insertion of the fluid ejection member 977 into the internal passage of the implant device 970, the plunger 980 may be pushed to advance the piston 978 to force treatment composition in the barrel of the syringe 974 to flow to and be ejected from the distal tip of the fluid ejection member 977. The fluid ejection member 977 may be inserted into the internal passage of the implant device 970 so that the distal tip of the fluid ejection member 977 is disposed in the internal passage when the treatment composition is ejected and the treatment composition is ejected into the internal passage from which the treatment composition may flow to the paranasal sinus. Alternatively, the injection member 977 may be inserted into the internal passage of the implant device 970 until the distal end of the injection member exits a distal end of the internal passage into the paranasal sinus, in which case the treatment composition may be ejected from the fluid ejection member 977 directly into the paranasal sinus.

The cutting tool 982 and the carrier tool 986 may have internal passages therethrough for insertion of a guide member (e.g., a guide wire). A kit may include such a guide wire or other guide member.

A variety of medical treatments and procedures may be performed through a paranasal sinus access implant device implanted to provide access to a paranasal sinus. Fluid treatment compositions may be administered to a paranasal sinus through the implant device. Fluid may be aspirated from a paranasal sinus through the implant device. One or more medical devices may be inserted into the paranasal sinus through the implant device.

The foregoing discussion of the invention and different aspects thereof has been presented for purposes of illustration and description. The foregoing is not intended to limit the invention to only the form or forms specifically disclosed herein. Consequently, variations and modifications commensurate with the above teachings, and the skill or knowledge of the relevant art, are within the scope of the present invention. The embodiments described hereinabove are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art. Although the description of the invention has included description of one or more possible implementations and certain variations and modifications, other variations and modifications are within the scope of the invention, e.g., as may be within the skill and knowledge of those in the art after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. Furthermore, any feature described or claimed with respect to any disclosed implementation may be combined in any combination with one or more of any other features of any other implementation or implementations, to the extent that the features are not necessarily technically incompatible, and all such combinations are within the scope of the present invention.

The terms "comprising", "containing", "including" and "having", and grammatical variations of those terms, are intended to be inclusive and nonlimiting in that the use of such terms indicates the presence of some condition or feature, but not to the exclusion of the presence also of any other condition or feature. The use of the terms "comprising", "containing", "including" and "having", and grammatical variations of those terms in referring to the presence of one or more components, subcomponents or materials, also include and is intended to disclose the more specific embodiments in which the term "comprising", "containing", "including" or "having" (or the variation of such term) as the case may be, is replaced by any of the narrower terms "consisting essentially of" or "consisting of" or "consisting of only" (or the appropriate grammatical variation of such narrower terms). For example, a statement that some thing "comprises" a stated element or elements is also intended to include and disclose the more specific narrower embodiments of the thing "consisting essentially of" the stated element or elements, and the thing "consisting of" the stated element or elements. Examples of various features have been provided for purposes of illustration, and the terms "example", "for example" and the like indicate illustrative examples that are not limiting and are not to be construed or interpreted as limiting a feature or features to any particular example. The term "at least" followed by a number (e.g., "at least one") means that number or more than that number. The term "at least a portion" means all or a portion that is less than all. The term "at least a part" means all or a part that is less than all.

The features in the drawings are shown for illustration purposes and to generally show relative positioning and interaction, and the features shown are not necessarily to scale.

What is claimed is:

1. A paranasal sinus access implant device for implantation in a human to fluidly connect a lacrimal apparatus from a location in an orbit to a paranasal sinus through a straight, surgically-formed fistula formed between the lacrimal apparatus in the orbit and the paranasal sinus, the implant device comprising:
   a proximal end at a first longitudinal end of the device;
   a distal end at a second longitudinal end of the device that is longitudinally opposite the first longitudinal end;
   a head adjacent the proximal end of the implant device;
   a conduit between the proximal end and the distal end and extending longitudinally along the implant device from adjacent the head toward the distal end of the implant device;
   an internal passage through the head and the conduit;
   a length of the implant device longitudinally along the implant device between the proximal end and the distal end in a range of from 8 millimeters to 50 millimeters;
   a width of the internal passage transverse to the length of the implant device in a range of from 0.25 millimeter to 5 millimeters;
   the conduit including a first longitudinal portion having a length of at least 3 millimeters and a second longitudinal portion having a length of at least 3 millimeters and being located toward the distal end relative to the first longitudinal portion;
   the first longitudinal portion of the conduit having a first minimum wall thickness adjacent the internal passage and the first longitudinal portion of the conduit extending from a proximal end of the first longitudinal portion of the conduit adjacent the head to a distal end of the first longitudinal portion of the conduit disposed toward a proximal end of the second longitudinal portion of the conduit;
   an exterior of the second longitudinal portion of the conduit having an anchoring surface feature including anchor protrusions spaced along the length of the second longitudinal portion of the conduit and recess areas between the anchor protrusions, the length of the second longitudinal portion of the conduit extending from a proximal end of the second longitudinal portion of the conduit at a said anchor protrusion closest to the head to a distal end of the second longitudinal portion of the conduit at a said anchor protrusion farthest from the head;
   the second longitudinal portion of the conduit having a second minimum wall thickness adjacent the internal passage that is smaller than the first minimum wall thickness, wherein the first minimum wall thickness is at least 0.05 millimeter larger than the second minimum wall thickness and the second minimum wall thickness is at a said recess area and occurs at multiple ones of the recess areas; and
   the implant device being configured to be implanted to fluidly connect the lacrimal apparatus to the paranasal sinus so that when implanted:
      the proximal end of the implant device and the head are disposed in the lacrimal apparatus;
      the distal end of the implant device is disposed in the paranasal sinus; and
      the conduit is disposed through the straight, surgically-formed fistula between the lacrimal apparatus and the paranasal sinus with at least a portion of each of the first longitudinal portion and the second longitudinal portion of the conduit disposed within the straight, surgically-formed fistula with multiple said anchor protrusions disposed within the straight, surgically-formed fistula to engage tissue within the straight, surgically-formed fistula and with the distal end of the second longitudinal portion of the conduit disposed in the paranasal sinus.

2. An implant device according to claim 1, wherein the length of the first longitudinal portion of the conduit is in a range of from 5 millimeters to 15 millimeters.

3. An implant device according to claim 2, wherein the first minimum wall thickness is in a range of from 0.35 millimeter to 0.55 millimeter.

4. An implant device according to claim 3, wherein the second minimum wall thickness is in a range of from 0.15 millimeter to 0.4 millimeter.

5. An implant device according to claim 4, wherein the first longitudinal portion of the conduit has a uniform wall thickness equal to the first minimum wall thickness over the entire length of the first longitudinal portion of the conduit.

6. An implant device according to claim 2, wherein the first longitudinal portion of the conduit has a smooth exterior surface over all of the exterior of the first longitudinal portion of the conduit.

7. An implant device according to claim 5, wherein the length of the second longitudinal portion of the conduit is in a range of from 5 millimeters to 15 millimeters.

8. An implant device according to claim 1, wherein the first longitudinal portion of the conduit has a first maximum exterior width that is at least 0.2 millimeters smaller than a second maximum exterior width of the second longitudinal portion of the conduit.

9. An implant device according to claim 8, wherein the first maximum exterior width is in a range of from 1.5 millimeters to 2.5 millimeters.

10. An implant device according to claim 8, wherein:
   the first longitudinal portion of the conduit has a first minimum exterior width that is the same as the first maximum exterior width, and the second longitudinal portion of the conduit has a second minimum exterior width;
   the second minimum exterior width is smaller than the first maximum exterior width; and
   the first minimum exterior width is larger than the second minimum exterior width.

11. An implant device according to claim 10, wherein:
the first maximum exterior width and the first minimum exterior width are each within a range of from 1.5 millimeters to 2.5 millimeters;
the second maximum exterior width is in a range of from 1.6 millimeters to 3 millimeters;
the second minimum exterior width is in a range of from 1 millimeter to 2 millimeters;
the first minimum exterior width is at least 0.1 millimeter larger than the second minimum exterior width; and
the second maximum exterior width is at least 0.2 millimeter larger than the first maximum exterior width.

12. An implant device according to claim 10, wherein:
the second minimum exterior width occurs at a location corresponding with the second minimum wall thickness.

13. An implant device according to claim 12, wherein:
the second maximum exterior width is in a range of from 1.6 millimeters to 3 millimeters; the second minimum exterior width is in a range of from 1 millimeter to 2 millimeters;
the first minimum exterior width is at least 0.1 millimeter larger than the second minimum exterior width; and
the second maximum exterior width is at least 0.2 millimeter larger than the first maximum exterior width.

14. An implant device according to claim 13, wherein:
the length of the first longitudinal portion is in a range of from 5 millimeters to 12 millimeters;
the length of the second longitudinal portion is in a range of from 5 millimeters to 20 millimeters; and
the conduit is constructed of polymeric material having a durometer (Shore A) in a range of from 50 to 100.

15. An implant device according to claim 14, wherein the anchoring surface feature is configured to anchor in the straight, surgically-formed fistula with the internal passage being straight through the entire length of the second longitudinal portion of the conduit when the implant device is implanted.

16. An implant device according to claim 15, wherein:
each said anchor protrusion comprises a separate circumferential ridge extending around an entire circumference of the conduit and the anchoring surface feature comprises at least 3 of the separate circumferential ridges.

17. An implant device according to claim 1, wherein:
the anchor protrusions have a height relative to the recess areas of at least 0.25 millimeter.

18. An implant device according to claim 17, wherein the length of the second longitudinal portion of the conduit is at least 5 millimeters along the length of the device between the said anchor protrusion closest to the head and the said anchor protrusion farthest from the head.

19. An implant device according to claim 1, wherein:
the head comprises a flanged tissue engagement surface on a side of the head disposed toward the conduit and configured to engage tissue outside of and adjacent to the straight, surgically-formed fistula when the implant device is implanted;
the head has a first dimension that is a maximum separation distance between points on the outer edge of the flanged tissue engagement surface, the first dimension being larger than an exterior width of the conduit defined by an extent of the anchor protrusions transverse to the length of the implant device;
wherein the head has a second dimension transverse to the first dimension that is a maximum separation distance between points on the outer edge that are on a line transverse to the first dimension, and a ratio of the first dimension to the second dimension in a range of from 1.5 to 4.

20. An implant device according to claim 1, wherein the length of the first longitudinal portion of the conduit is in a range of from 5 millimeters to 12 millimeters and the length of the second longitudinal portion of the conduit is in a range of from 5 millimeters to 20 millimeters.

21. An implant device according to claim 1, wherein the conduit is constructed of polymeric material having a durometer (Shore A) in a range of from 50 to 100.

22. A kit for use to treat a paranasal sinus, the kit comprising:
a paranasal sinus access implant device according to claim 1; and
at least one additional component useful in connection with implantation of the implant device or performance of a medical treatment or procedure through the implant device.

23. A kit according to claim 22, comprising a fluid treatment composition deliverable to a paranasal sinus through the implant device following implantation of the implant device to provide access to the paranasal sinus.

24. A kit according to claim 23, wherein the treatment composition is contained in a fluid container of a fluid dispenser manipulable to dispense at least a portion of the treatment composition from the fluid container into the internal passage or through the internal passage directly into a paranasal sinus following implantation of the implant device;
the fluid dispenser comprises a fluid ejection member in fluid communication with the treatment composition in the fluid container, the fluid ejection member being insertable in the internal passage of the implant device; and
the fluid dispenser is manipulable when the fluid ejection member is inserted in the internal passage of the implant device when the implant device is implanted to eject at least a portion of the treatment composition from a distal end of the fluid ejection member into the internal passage or distal of the internal passage directly into a paranasal sinus.

25. A kit according to claim 24, wherein the fluid ejection member has an insertion portion configured to be inserted into the internal passage and the insertion portion has a maximum outside width of no larger than 1.5 millimeters.

26. A kit according to claim 23, wherein the treatment composition is an aqueous irrigation liquid.

27. A kit according to claim 23, wherein the treatment composition is a drug treatment composition.

28. A kit according to claim 27, wherein the drug treatment composition comprises at least one drug for treating sinusitis.

29. A kit according to claim 27, wherein the drug treatment composition comprises any one or more of the following in any combination: an antibiotic, a steroid, an anti-viral, an antihistamine, an anti-fungal, a mast cell stabilizer, a mucolytic, a non-steroidal anti-inflammatory drug (NSAID), a vasoconstrictor, and an immunosuppressant.

30. A kit according to claim 27, wherein the fluid container contains a volume of the treatment composition in a range of from 0.1 milliliters to 3 milliliters.

31. A kit according to claim 22, comprising at least one cutting tool for cutting away tissue to form a fistula through which the implant device may be implanted during an implantation procedure.

32. A kit according to claim 31, wherein the at least one cutting tool comprises a hollow cutting member having a hollow cutting tip at a distal end of the cutting member configured to cut tissue to size the fistula for implantation of the implant device through the fistula.

33. A kit according to claim 32, wherein the cutting member has a cutting width that is smaller than a maximum exterior width of a conduit of the implant device configured to be disposed through the fistula during implantation.

34. A kit according to claim 33, wherein the cutting width is not more than 0.75 millimeter smaller than the maximum exterior width of the conduit.

35. A kit according to claim 34, wherein the cutting width is in a range of from 1.5 millimeters to 2.5 millimeters and the maximum exterior width of the conduit of the implant device is in a range of from 2.0 to 2.75 millimeters.

36. A kit according to claim 22, comprising a carrier tool for carrying the implant device during an implantation procedure, the carrier tool comprising:
   a carrier member with a distal tip, the carrier member being adapted to be disposed through a fistula between the lacrimal apparatus in the orbit and a paranasal cavity with the distal tip located in the paranasal cavity; and
   a hand-manipulable handle connected to the carrier member;
   wherein:
   the implant device is mountable on the carrier member for implantation with the mounted implant device disposed between the handle and the distal tip with the carrier member disposed through the internal passage and with a proximal end of the implant device disposed toward the handle and a distal end of the implant device disposed toward the distal tip of the member; and
   when the implant device is mounted for implantation, the carrier is disengageable from the implant device for implant placement of the implant device during an implantation procedure to provide fluid access to a paranasal sinus.

37. A kit according to claim 22, comprising:
   at least one cutting tool for cutting away tissue to form a fistula through which the implant device may be implanted during an implantation procedure;
   a carrier tool for carrying the implant device during an implantation procedure, the carrier tool comprising:
      a carrier member with a distal tip, the carrier member being adapted to be disposed through a fistula between the lacrimal apparatus in the orbit and a paranasal cavity with the distal tip located in the paranasal cavity; and
      a hand-manipulable handle connected to the carrier member;
      wherein:
      the implant device is mountable on the carrier member for implantation with the mounted implant device disposed between the handle and the distal tip with the carrier member disposed through the internal passage and with a proximal end of the implant device disposed toward the handle and a distal end of the implant device disposed toward the distal tip of the member; and
      when the implant device is mounted for implantation, the carrier is disengageable from the implant device for implant placement of the implant device during an implantation procedure to provide fluid access to a paranasal sinus; and
   a guide member having a distal end configured to be disposed in or distal of a fistula formed between the lacrimal apparatus and the paranasal sinus;
   wherein:
   the cutting tool comprises an internal passage through which the guide member may be inserted such that cutting tool may slidably engaged with the guide member while the distal end of the guide member is disposed in the fistula; and
   the carrier tool comprises an internal passage through which the guide member may be inserted while the distal end of the guide member is disposed in the fistula to guide the carrier tool to the site of the fistula for implantation of the implant device.

38. An implant device according to claim 1, wherein the said anchor protrusion closest to the head is disposed along the length of the implant device at least 3 millimeters from the head.

* * * * *